United States Patent [19] [11] 4,091,210
Kamiya et al. [45] May 23, 1978

[54] PREPARATION OF 3-ALKYL-3-CEPHEM-4-CARBOXYLIC ACID COMPOUNDS FROM DITHIO ISOPROPENYL AZETIDINE CARBOXYLIC COMPOUNDS

[75] Inventors: Takashi Kamiya, Suita; Tsutomu Teraji; Masashi Hashimoto, both of Toyonaka; Osamu Nakaguti, Osaka; Teruo Oku, Kyoto, all of Japan

[73] Assignee: Fujisawa Pharmaceutical Co., Ltd., Osaka, Japan

[21] Appl. No.: 674,234

[22] Filed: Apr. 6, 1976

Related U.S. Application Data

[63] Continuation-in-part of Ser. No. 401,145, Sep. 27, 1973, abandoned.

[30] Foreign Application Priority Data

Oct. 20, 1972 Japan .................................. 47-105558
Nov. 27, 1972 Japan .................................. 47-119114
Dec. 13, 1972 Japan .................................. 47-125574

[51] Int. Cl.² .......................................... C07D 501/02
[52] U.S. Cl. ................................. 544/18; 260/239 A; 424/246
[58] Field of Search ....................... 260/243 C; 544/18

[56] References Cited

U.S. PATENT DOCUMENTS

| 3,275,626 | 9/1966 | Morin et al. | 260/243 C |
| 3,725,397 | 4/1973 | Graham et al. | 260/243 C |
| 3,725,399 | 4/1973 | Ellerton et al. | 260/243 C |
| 4,024,152 | 5/1977 | Kukolja | 260/243 C |

FOREIGN PATENT DOCUMENTS 25,188/72  10/1972  Japan ....................................... 544/18

OTHER PUBLICATIONS

Smolinsky et al., JACS vol. 86 (Aug. 5, 1964), p. 3085.
Abramovitch et al., Chem. vol. 64, 1964, pp. 156, 157, 169–171.

*Primary Examiner*—Nicholas S. Rizzo

*Attorney, Agent, or Firm*—Oblon, Fisher, Spivak, McClelland & Maier

[57] ABSTRACT

A new process for preparing 3-alkyl-3-cephem-4-carboxylic acids of the general formula:

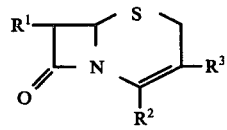

wherein $R_1$ is amino or a substituted amino, $R^2$ is carboxy or a protected carboxy and $R^3$ is a lower alkyl, and new intermediates of the general formula:

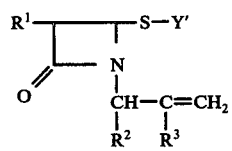

wherein $R^1$, $R^2$ and $R^3$ are each as defined above and $Y'$ is a residue of ammonia or a saturated aliphatic amine or a secondary cyclic amine, comprises reacting a compound of the formula

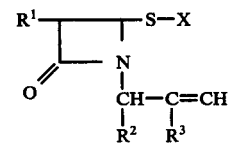

wherein X is a residue of a thiol compound, with a condensing agent or a polar solvent, or with ammonia or an amine, respectively. In the latter case, the resultant new intermediate may further be reacted with a condensing agent or a polar solvent to form a 3-alkyl-3-cephem-4-carboxylic acid as above.

4 Claims, No Drawings

PREPARATION OF 3-ALKYL-3-CEPHEM-4-CARBOXYLIC ACID COMPOUNDS FROM DITHIO ISOPROPENYL AZETIDINE CARBOXYLIC COMPOUNDS

CROSS REFERENCE TO RELATED APPLICATIONS

This application is a continuation-in-part of application Ser. No. 401,145, filed Sept. 27, 1973, now abandoned.

This invention relates to a process for preparing 3-alkyl-3-cephem-4-carboxylic acid and intermediates thereof.

According to this invention there is provided new processes for preparing 3-alkyl-3-cephem-4-carboxylic acids which are shown in the following scheme.

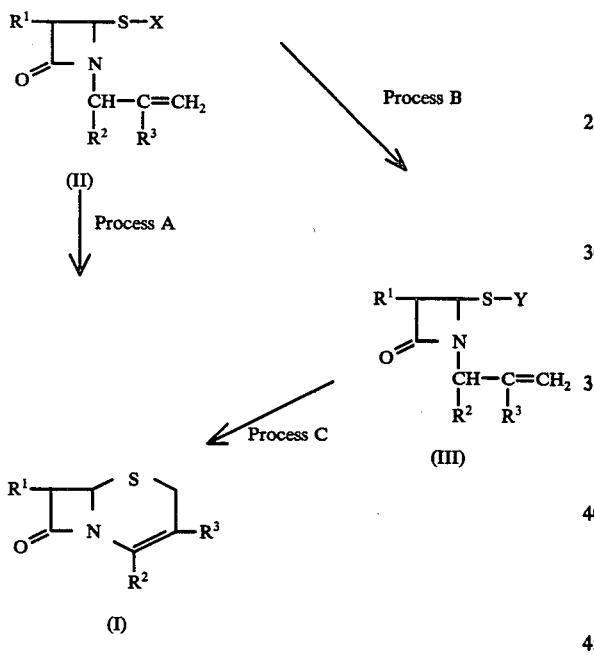

wherein $R^1$ is amino or a substituted amino, $R^2$ is carboxy or a protected carboxy, $R^3$ is a lower alkyl, X is a residue of a thiol compound HX and Y is a residue of ammonia or an amine.

This invention provides new processes for preparing 3-alkyl-3-cephem-4-carboxylic acids (I), which are known compounds exhibiting antibacterial properties, and new intermediates used for preparing 3-alkyl-3-cephem-4-carboxylic acid (I).

The new intermediates provided in this invention are represented by the general formula:

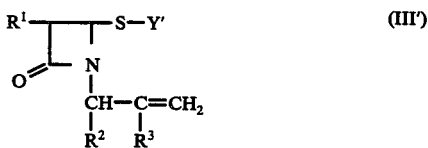

wherein $R^1$, $R^2$ and $R^3$ are each as defined above and $Y'$ is a residue of ammonia or a saturated aliphatic amine or a secondary cyclic amine, which are included in the intermediates (III) produced by the process (B) as illustrated above.

The compounds (II) to be used as the starting compounds in the processes of this invention may be prepared by reacting the corresponding 2-methyl-2-lower alkyl-6-substituted penam-3-carboxylic acid -1-oxide compounds with the corresponding thiol compounds In the above and subsequent description, the term "a substituted amino" for $R^1$ means suitable substituted amino groups which include;

suitable substituted amino groups include hydrazino, mono(or di-)-(lower)alkylamino, mono(or di-)-(lower) alkenylamino, lower alkylideneamino, phenyl(lower)-alkylideneamino, acylamino and amino group substituted with other amino protecting groups than the acyl groups; suitable lower alkyl groups in the mono (or di-)-(lower) alkylamino include methyl, ehtyl, propyl, isopropyl, butyl, etc.;

suitable lower alkenyl groups in the mono(or di-)-(lower)-alkenylamino include allyl, 2-butenyl, etc.;

suitable lower alkylidene groups in the lower alkylideneamino include ethylidene, propylidene, butylidene, etc.;

suitable alklidene include benzylidene, phenethylidene, etc.;

suitable acyl groups in the acylamino groups include carbamoyl, aliphatic acyl groups and acyl groups containing an aromatic or heterocyclic ring;

suitable aliphatic acyl groups include saturated or unsaturated, lower or higher alkanoyl groups which may be branched or which may contain a cyclic ring, such as lower or higher aliphatic acyl groups, for example, lower alkanoyl (e.g., formyl, acetyl, propionyl, butyryl, isobutyryl, valeryl, isovaleryl, oxalyl, succinyl, pivaloyl, etc.), higher alkanoyl (e.g., octanoyl, lauroyl, palmitoyl, etc.), lower alkenoyl (e.g., acryloyl, crotonoyl, etc.), lower alkynoyl (e.g., propynoyl, etc.), lower or higher cycloalkanecarbonyl (e.g., cyclopentanecarbonyl, cyclohexanecarbonyl, cycloheptanecarbonyl, etc.), lower or higher cycloalkyl(lower)alkanoyl cyclopentylacetyl, cyclohexylacetyl, cycloheptylacetyl, cyclohexylpropionyl, cycloheptylpropionyl, etc.), dihydrobenzoyl, dihydrophenyl(lower)alkanoyl (e.g., dihydrophenylacetyl, dihydrophenylpropionyl, etc.), etc., and lower or higher aliphatic acyl groups containing a oxygen or sulfur atom, for example, lower alkoxy(lower)alkanoyl (e.g., methoxyacetyl, ethoxyacetyl, methoxypropionyl, etc.), lower alkylthio(lower)alkanoyl (e.g., methylthioacetyl, ethylthioacetyl, methylthiopropionyl, etc), lower alkenylthio(lower)alkanoyl (e.g., allylthioacetyl, allylthiopropionyl, etc.), lower or higher cycloalkylthio (lower)alkanoyl (e.g., cyclopentylthioacetyl, cyclohexylthiopropionyl, cycloheptylthioacetyl, etc.), lower or higher cycloalkoxy(lower)alkanoyl (e.g., cyclopentyloxyacetyl, cyclohexyloxypropionyl, etc.), dihydrophenoxy(lower)alkanoyl dihydrophenoxyacetyl, dihydrophenoxypropionyl, etc.), dihydrophenylthio(lower)alkanoyl (e.g., dihydrophenylthioacetyl, dihydrophenylthiopropionyl, etc.), lower alkoxycarbonyl (e.g., methoxycarbonyl, ethoxycarbonyl, propoxycarbonyl, 1-cyclopropylethoxycarbonyl, isopropoxycarbonyl, butoxycarbonyl, tertiarybutoxycarbonyl, etc.), lower or higher cycloalkyloxycarbonyl (e.g., cyclopentyloxycarbonyl, cyclohexyloxycarbonyl, cycloheptyloxycarbonyl, etc.), lower or higher cycloalkyl(lower)alkoxycarbonyl 1- cyclopropylethoxycarbonyl, etc.), dihydrophenoxycarbonyl;

suitable acyl groups containing an aromatic ring such as benzene, naphthalene and the like, include, for example, phenylcarbamoyl, benzoyl, toluoyl, naphthoyl, α-methylnaphthoyl, phthaloyl, benzenesulfonyl, tetrahydronaphthoyl, indancarbonyl, phenyl(lower)alkanoyl (e.g., phenylacetyl, phenylpropionyl, phenylbutyryl, etc.), tolyl(lower)alkanoyl (e.g., tolylacetyl, etc.), xylyl(lower)alkanoyl (e.g., xylylacetyl, etc.), naphthyl(lower)alkanoyl (e.g., naphthylacetyl, etc.), tetrahydronapthyl(lower)alkanoyl (e.g., tetrahydronaphthylacetyl, etc.), indanyl(lower)alkanoyl (e.g., indanylacetyl, etc.), phenoxy(lower)alkanoyl (e.g., phenoxyacetyl, phenoxypropionyl, phenoxybutyryl, etc.), xylyloxy(lower)alkanoyl (e.g., xylyloxyacetyl, etc.), phenoxycarbonyl, xylyloxycarbonyl, naphthyloxycarbonyl, indanyloxycarbonyl, phenyl(lower)alkoxycarbonyl (e.g., benzyloxycarbonyl, phenethyloxycarbonyl, etc.), phenylthio(lower)alkanoyl (e.g., phenylthioacetyl, phenylthiopropionyl, etc.), phenylglyoxyloyl, etc;

suitable acyl groups containing an heterocyclic ring include, for example, heterocylic carbonyl, heterocyclic lower alkanoyl, heterocyclic lower alkoxycarbonyl, heterocyclic-oxycarbonyl, heterocyclic-oxy(lower)alkanoyl, heterocyclic-thio(lower)alkanoyl, etc. wherein said heterocyclic moiety may be saturated or unsaturated, monocyclic or polycyclic, and may contain at least one hetero-atom, such as an oxygen, sulfur, nitrogen atom or the like, for example, unsaturated 3 to 8-membered heteromonocyclic containing a sulphur atom (e.g., thienyl, etc.), unsaturated condensed-heterocyclic containing a sulfur atom (e.g., benzothienyl, etc.), unsaturated 3 to 8-membered heteromonocyclic containing an oxygen atom (e.g., furyl, 2-(or 4-)pyranyl, 5,6-dihydro-2H-pyran-3-yl, etc.), unsaturated 3 to 8-membered heteromonocyclic containing 1 to 4 nitrogen atom(s) (e.g, pyrrolyl, 2(or 3)H-pyrrolyl, 2(or 3)-pyrrolinyl, imidazolyl, pyrazolyl, pyridyl, pyrimidyl, pyrazinyl, pyridazinyl, 1H-tetrazolyl, 2H-tetrazolyl, etc.), saturated 3 to 8-membered heteromonocyclic containing 1 to 2 nitrogen atom(s) (e.g., pyrrolidinyl, imidazolidinyl, piperidino, piperadinyl, etc.), unsaturated condensed-heterocyclic containing 1 to 3 nitrogen atom(s) (e.g., indolyl, isoindolyl, indolizinyl, benzimidazolyl, quinolyl, isoquinolyl, 1(or 2)H-indazolyl, 1(or 2)H-benzotriazolyl, etc.), unsaturated 3 to 8-membered heteromonocyclic containing an oxygen atom(s) and 1 to 3 nitrogen atom(s) (e.g., oxazolyl, isoxazolyl, oxadiazolyl, etc.), saturated 3 to 8 membered heteromonocyclic containing 1 to 2 oxygen atom(s) and 1 to 2 nitrogen atom(s) (e.g., sydnonyl, etc.), unsaturated 3 to 8-membered heteromonocyclic containing a sulfur atom and 1 to 3 nitrogen atom(s) (e.g., thiazolyl, thiadiazolyl, etc.), unsaturated condensed-heterocyclic containing an oxygen atom and 1 to 2 nitrogen atom(s) (e.g., benzoxazolyl, benzoxadiazolyl, etc.), unsaturated condensed-heterocyclic containing a sulfur atom and 1 to 2 nitrogen atom(s) (e.g., benzothiazolyl, benzothiadiazolyl, etc.), etc.;

the carbamoyl, the aliphatic acyl groups and the acyl groups containing an aromatic or heterocyclic ring may have 1 to 10 appropriate substituent(s) such as lower alkyl(e.g., methyl, ethyl, propyl, isopropyl, etc.), lower alkenyl (e.g., 1-propenyl, allyl, etc.), lower or higher cycloalkyl (e.g., cyclopropyl, cyclopentyl, cyclohexyl, cycloheptyl, etc.), lower alkoxy (e.g., methoxy, ethoxy, propoxy, isopropoxy, etc.), lower alkylthio (e.g., methylthio, ethylthio, etc.), aryl(e.g., phenyl, xylyl, tolyl, indanyl, etc.), phenyl(lower)alkyl (e.g., benzyl, phenethyl, etc.), halogen (e.g., chlorine, bromine, fluorine, etc.), halophenyl (e.g., chlorophenyl, bromophenyl, etc.), halophenoxy (e.g., chlorophenoxy, bromophenoxy, etc.), cyano, lower alkylsulfinyl (e.g., methylsulfinyl, ethylsulfinyl, etc.), lower alkanesulfonyl (e.g., methanesulfonyl, ethanesulfonyl, etc.), lower alkoxycarbonyl(lower)alkoxy (e.g., methoxycarbonylmethoxy, ethoxycarbonyleth0xy, tertiarybutoxycarbonylmethoxy, etc.), nitro, sulfo, amino, azido, mercapto, carboxy, hydroxy, hydroxyamino, mono(or di)alkylamino [e.g., mono(or di)methylamino, mono(or di)ethylamino, mono(or di)-propylamino, mono(or di) isopropylamino, etc.], lower or higher cycloalkyl(lower)alkoxycarbonyl(lower)alkoxy (e.g., 1-cyclopropylethoxycarbonylmethoxy, etc.); acetyl, when the acyl group has a functional group, such as amino, hydroxy, mercapto, carboxy, etc., the functional group may be protected with an appropriate protective group; suitable protective group for the amino group include any of the conventional protective groups, for example, the acyl groups or other groups than the acyl groups such as trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxocyclohexylidene (among these, 1-methoxycarbonyl-2-propylidene and 2-ethoxycarbonylcyclohexylidene radicals may be representable as 1-methoxycarbonyl-1-propene-2-yl and 2-ethoxycarbonyl-1-cyclohexenyl radical, respectively), mono or disilyl, etc.;

suitable protective groups for hydroxy or mercapto groups include any of the conventional protective groups for hydroxy or mercapto groups, for example, the acyl groups or other groups than the acyl group such as benzyl, trityl, methoxymethyl, 2-nitrophenylthio, 2,4-dinitrophenylthio, etc.;

suitable protective groups for the carboxy group may be any of those conventional protective groups used for protecting a carboxy group, for example, lower alkyl ester (e.g., methyl ester, ethyl ester, propyl ester, butyl ester, 1-cyclopropylethyl ester, tertiarybutyl ester, etc.), mono(or di or tri)halo(lower)alkyl ester (e.g., chloromethyl ester, 2,2,2-trichloroethyl ester, 3,3-dibromopropyl ester, etc.), aryl ester (e.g., phenyl ester, nitrophenyl ester, indanyl ester, etc.), ar(lower)alkyl ester (e.g., benzyl ester, diphenylmethyl ester, triphenylmethyl ester, p-nitrobenzyl ester, p-bromobenzyl ester, etc.), tri(lower)alkylsilyl ester (e.g., trimethylsilyl ester, triethylsilyl ester, etc.) etc.; the amino protective group other than an acyl group which is mentioned in the substituted amino group is the same as that which is exemplified as the protective group for the amino radical in the acyl group; particularly suitable acyl groups include:

(1) lower alkoxycarbonyl (e.g., methoxycarbonyl, ethoxycarbonyl, propoxycarbonyl, 1-cyclopropylethoxycarbonyl, butoxycarbonyl, tertiarybutoxycarbonyl, etc.), (2) lower alkylthio(lower)alkanoyl (e.g., 2-methylthioacetyl, 2-ethylthioacetyl, 3-methylthiopropionyl, etc.), (3) lower alkenylthio(lower)alkanoyl (e.g., 2-allylthioacetyl, 3-allylthiopropionyl, etc.)

(4) cyano(lower)alkanoyl (e.g., 2-cyanoacetyl, 3-cyanopropionyl, 4-cyanobutyryl, etc.), (5) phenyl(lower)alkanoyl (e.g., 2-phenylacetyl, 3-phenylpropionyl, 4-phenylbutyryl, etc.), (6) phenoxy(lower)alkanoyl (e.g., 2-phenoxyacetyl, 3-phenoxypropionyl, 4-phenoxybutyryl, etc.), (7) phenylcarbamoyl, (8) phenylglyoxyloyl, (9) phenylthiocarbonyl,

(10) phenyl and amino substituted lower alkanoyl (e.g., phenylglycyl, 3-amino-3-phenylpropionyl, etc.),

(11) phenyl and hydroxy substituted lower alkanoyl (e.g., 2-hydroxy-2-phenylacetyl, 2-hydroxy-3-phenylpropionyl, etc.),

(12) phenyl and lower alkoxycarbonylamino substituted lower alkanoyl (e.g., N-methoxycarbonylphenylglycyl, N-ethoxycarbonylphenylglycyl, N-(1-cyclopropylethoxy)carbonyl-phenylglycyl, N-tertiarybutoxycarbonylphenyglycyl, 2-(1-cyclopropylethoxy)carbonylamino-3-phenylpropionyl, etc.),

(13) phenyl and trihalo(lower)alkoxycarbonylamino substituted lower alkanoyl (e.g., N-trichloroethoxycarbonylphenylglycyl, 3-trichloroethoxycarbonylamino-3-phenylpropionyl, N-tribromoethoxycarbonylphenylglycyl, etc.),

(14) phenyl and lower alkanoyloxy substituted lower alkanoyl (e.g., 2-formyloxy-2-phenylacetyl, 2-acetoxy-2-phenylacetyl, 3-propionyloxy-3-phenylpropionyl, etc.),

(15) phenyl and semicarbazono substituted lower alkanoyl (e.g., 2-phenyl-2-semicarbazonoacetyl, 2-semicarbazono-3-phenylpropionyl, etc.),

(16) halophenylthiocarbamoyl (e.g., 2-(or 3 or 4-)chlorophenylthiocarbamoyl, 2-(or 3- or 4-)chlorophenylthiocarbamoyl, 2-(or 3- or 4-)bromophenylthiocarbamoyl, etc.),

(17) phthaloyl,

(18) lower alkanoylaminobenzenesulfonyl (e.g., 2-(or 3- or 4-)acetamidobenzenesulfonyl, 2-(or 3- or 4-)propionamidobenzenesulfonyl, etc.),

(19) phenyl and halophenoxy substituted lower alkanoyl (e.g., 2-phenyl-2-[2-(or 3- or 4-)chlorophenoxy]acetyl, 2-phenyl-2-[2-(or 3- or 4-)bromophenoxy]acetyl, etc.),

(20) halophenyl(lower)alkanoyl (e.g., 2-[2-(or 3- or 4-)chlorophenyl]acetyl, 2-[2-(or 3- or 4-)bromophenyl]acetyl, 3-[2-(or 3- or 4-)chlorophenyl]propionyl, etc.),

(21) phenyl(lower)alkoxycarbonyl (e.g., benzyloxycarbonyl, phenethyloxycarbonyl, etc.),

(22) hydroxyphenyl and amino substituted lower alkanoyl (e.g., 2-amino-2-[2-(or 3- or 4-)hydroxyphenyl]acetyl, 2-amino-3-[2-(or 3- or 4-)hydroxyphenyl]propionyl, etc.),

(23) hydroxyphenyl and lower alkoxycarbonylamino substituted lower alkanoyl (e.g., 2-methoxycarbonylamino-2-[2-(or 3- or 4-)hydroxyphenyl]acetyl, 2-(1-cyclopropylethoxy)carbonylamino-2-[2-(or 3- or 4-) hydroxyphenyl]acetyl, 2-tertiarybutoxycarbonylamino-2-[2-(or 3- or 4-)hydroxyphenyl]acetyl, etc.),

(24) phenyl and sulfo substituted lower alkanoyl (e.g., 2-phenyl-2-sulfoacetyl, 3-phenyl-3-sulfopropionyl, etc.),

(25) lower alkoxyphenyl and amino substituted lower alkanoyl (e.g., 2-amino-2-[2-(or 3- or 4-)methoxyphenyl]acetyl, 2-amino-3-[2-(or 3- or 4-)methoxyphenyl]acetyl, etc.),

(26) lower alkoxyphenyl and lower alkoxycarbonylamino substituted lower alkanoyl (e.g., 2-methoxycarbonylamino-2-[2-(or 3- or 4-)methoxyphenyl]acetyl, 2-(1-cyclopropylethoxy)carbonylamino-2-[2-(or 3- or 4-)methoxyphenyl]acetyl, 2-tertiarybutoxycarbonylamino-2-[2-(or 3- or 4-)methoxyphenyl]acetyl, etc.),

(27) lower alkylthiophenyl and amino substituted lower alkanoyl (e.g., 2-amino-2-[2-(or 3- or 4-)methylthiophenyl]acetyl, 2-amino-3-[2-(or 3- or 4-)ethylthiophenyl]propionyl, etc.),

(28) lower alkylthiophenyl and lower alkoxycarbonylamino substituted lower alkanoyl (e.g., 2-methoxycarbonylamino-2-[2-(or 3- or 4-)methylthiophenyl]acetyl, 2-(1-cyclopropylethoxy)carbonylamino-2-[2-(or 3- or 4-)methylthiophenyl]acetyl, 2-tertiarybutoxycarbonylamino-2-[2-(or 3- or 4-)methylthiophenyl]acetyl, 2-tertiarybutoxycarbonylamino-3-[2-(or 3- or 4-)ethylthiophenyl]propionyl, etc.),

(29) lower alkylsulfinylphenyl and amino substituted lower alkanoyl (e.g., 2-amino-2-[2-(or 3- or 4-)methylsulfinylphenyl]acetyl, 2-amino-3-[2-(or 3- or 4-)ethylsulfinylphenyl]propionyl, etc.),

(30) lower alkylsulfinylphenyl and lower alkoxycarbonylamino substituted lower alkanoyl (e.g., 2-methoxycarbonylamino-2-[2-(or 3- or 4-)methylsulfinylphenyl]acetyl, 2-(1-cyclopropylethoxy)carbonylamino-3-[2-(or 3- or 4-)ethylsulfinylphenyl]propionyl, 2-tertiarybutoxycarbonylamino-2-[2-(or 3- or 4-)methylsulfinylphenyl]acetyl, etc.).

(31) lower alkoxycarbonyl(lower)alkoxyphenyl and amino substituted lower alkanoyl (e.g., 2-amino-2-[2-(or 3- or 4-)methoxycarbonylmethoxyphenyl]acetyl, 2-amino-3-[2-(or 3- or 4-)propoxycarbonylmethoxyphenyl]propionyl, 2-amino-2-[2-(or 3- or 4-)tertiarybutoxycarbonylmethoxyphenyl]acetyl, etc.),

(32) lower alkoxycarbonyl(lower)alkoxyphenyl and lower alkoxycarbonylamino substituted lower alkanoyl (e.g., 2-methoxycarbonylamino-2-[2-(or 3- or 4-)methoxycarbonylmethoxyphenyl]acetyl, 2-(1-cyclopropylethoxy)carbonyl-3-[2-(or 3- or 4-)ethoxycarbonylmethoxyphenyl]propionyl, 2-tertiarybutoxycarbonylamino-2-[2-(or 3- or 4-)tertiarybutoxycarbonylmethoxyphenyl]acetyl, etc.),

(33) phenyl and thiadiazolythio(lower)alkanoylamino substituted lower alkanoyl (e.g., N-(1,3,4-thiadiazol-2-yl)thioacetylphenylglycyl, 2-[3-(1,3,4-thiadiazol-2-yl)thiopropionyl]amino-3-phenylpropionyl, etc.),

(34) phenyl and indanyloxycarbonyl substituted lower alkanoyl (e.g., 2-phenyl-2-indanyloxycarbonylacetyl, 3-phenyl-2-indanyloxycarbonylpropionyl, etc.),

(35) dihydrophenyl and amino substituted lower alkanoyl (e.g., 2-amino-2-(2,5-dihydrophenyl)acetyl, 2-amino-3-(2,5-dihydrophenyl)propionyl, etc.),

(36) dihydrophenyl and lower alkoxycarbonylamino substituted lower alkanoyl (e.g., 2-methoxycarbonylamino-2-(2,5-dihydrophenyl)acetyl, 2-(1-cyclopropylethoxy)carbonylamino-2-(2,5-dihydrophenyl)acetyl, 2-tertiarybutoxycarbonylamino-2-(2,5-dihydrophenyl)acetyl, 2-tertiarybutoxycarbonylamino-3-(2,5-dihydrophenyl)propionyl, etc.),

(37) 3-halophenyl-5-lower alkylisoxazol-4-ylcarbonyl (e.g., 3-[2-(or 3- or 4-)chlorophenyl]-5-methylisoxazol- 4-ylcarbonyl, 3-[2-(or 3- or 4-)bromophenyl]-5-ethylisoxazol-4-ylcarbonyl, etc.),

(38) thienyl(lower)alkanoyl (e.g., 2-(2-thienyl)acetyl, 3-(2-thienyl)propionyl, etc.),

(39) thienyl and amino substituted lower alkanoyl (e.g., 2-amino-2-(2-thienyl)acetyl, 2-amino-3-(2-thienyl)propionyl, etc.),

(40) thienyl and lower alkoxycarbonylamino substituted lower alkanoyl (e.g., 2-methoxycarbonylamino-2-(2-thienyl)acetyl, 2-(1-cyclopropylethoxy)carbonylamino-2-(2-thienyl)acetyl, 2-tertiarybutoxycarbonylamino-2-(2-thienyl)acetyl, 2-tertiarybutoxycarbonylamino-3-(2-thienyl)propionyl, etc.),

(41) tetrazolyl(lower)alkanoyl (e.g., 2-(1H-tetrazol-1-yl)acetyl, 3-(1H-tetrazol-1-yl)propionyl, 4-(1H-tetrazol-1-yl)butyryl, etc.),

(42) thiadiazolyl(lower)alkanoyl (e.g., 2-(1,2,5-thiadiazol-3yl)acetyl, 2-(1,3,4-thiadiazol-2-yl)acetyl, 3-(1,2,5-thiadiazol-3-yl)propionyl, etc.),

(43) thiadiazolylthio(lower)alkanoyl (e.g., 2-(1,3,4-thiadiazol-2-ylthio)acetyl, 2-(1,2,5-thiadiazol-3-ylthio)acetyl, 3-(1,3,4-thiadiazol-2-ylthio)propionyl, etc.),

(44) halobenzotriazolyl(lower)alkanoyl (e.g., 2-[4-(or 5- or 6- or 7-)chloro-1H-benzotriazol-1-yl]acetyl, 2-[4-(or 5- or 6- or 7-)bromo-1H-benzotriazol-1-yl]-acetyl, 3-[4-(or 5- or 6- or 7-)fluoro-2H-benzotriazol-2-yl]propionyl, etc.),

(45) lower alkylthiadiazolyloxy(lower)alkanoyl (e.g., 2-(5-methyl-1,3,4-thiadiazol-2-yloxy)acetyl, 2-(4-methyl-1,2,5-thiadiazol-3-yloxy)acetyl, 2-(5-ethyl-1,3,4-thiadiazol-2-yloxy)propionyl, etc.),

(46) dihydropyranyl and amino substituted lower alkanoyl (e.g., 2-amino-2-(5,6-dihydro-2H-pyran-3-yl)acetyl, 2-amino-3-(5,6-dihydro-2H-pyran-3-yl)propionyl, etc.)

(47) dihydropyranyl and lower alkoxycarbonylamino substituted lower alkanoyl (e.g., 2-methoxycarbonylamino-2-(5,6-dihydro-2H-pyran-3-yl)acetyl, 2-(1-cyclopropylethoxy)carbonylamino-2-(5,6-dihydro-2H-pyran-3-yl)acetyl, 2-tertiarybutoxycarbonylamino-2-(5,6-dihydro-2H-pyran-3-yl)acetyl, 2-tertiarybutoxycarbonylamino-3-(5,6-dihydro-2H-pyran-3-yl)propionyl, etc.), and

(48) sydonyl(lower)alkanoyl (e.g., 2-(sydnon-3yl)acetyl, 3-(sydnon-3-yl)propionyl, etc);

the term "a protected carboxy group" for $R_2$ includes ester, acid amide, acid anhydride, salt, etc.;

suitable esters include silyl esters, aliphatic esters and esters containing an aromatic or heterocyclic ring;

suitable silyl esters such as tri(lower)alkylsilyl (e.g., trimethylsilyl, triethylsilyl, etc.) esters, etc.;

suitable aliphatic esters include saturated or unsaturated, lower or higher alkyl esters which may be branched or which may contain a cyclic ring, such as lower or higher aliphatic esters, for example, lower alkyl (e.g., methyl, ethyl, propyl, isopropyl, butyl, tertiarybutyl, etc) ester, lower or higher cycloalkyl(lower)alkyl (e.g., 1-cyclopropylethyl, etc.) esters lower alkenyl (e.g., vinyl, 1-propenyl, allyl, 3-butenyl, etc.) esters, lower alkynyl (e.g., 3-butynyl, 4-pentynyl, etc.) esters, lower or higher cycloalkyl (e.g., cyclopentyl, cyclohexyl, cycloheptyl, etc.) esters, etc., and lower or higher aliphatic esters containing a nitrogen, sulfur or oxygen atom, for example, lower alkoxy(lower)alkyl (e.g., methoxymethyl, ethoxyethyl, methoxyethyl, etc.) esters, lower alkylthio(lower)alkyl (e.g., methylthiomethyl, ethylthioethyl, methylthiopropyl, etc.) esters, di(lower)alkylamino (e.g., dimethylamino, diethylamino, dipropylamino, etc.) esters, lower alkylidinamino (e.g., ethylideneamino, propylideneamino, isopropylideneamino, etc.) esters, lower alkylsulfenyl (lower)alkyl (e.g., methylsulfenylmethyl, ethylsuflenymethyl, etc.) esters, etc.;

suitable esters containing an aromatic ring include, for example, aryl (e.g., phenyl, xylyl, tolyl, naphthyl, indanyl, dihydroanthryl, etc.) esters, phenyl(lower)alkyl (e.g., benzyl, phenethyl, etc.) esters, phenoxy(lower)alkyl(phenoxymethyl, phenoxyethyl, phenoxypropyl, etc.) esters, phenylthio(lower)alkyl (e.g., phenylthiomethyl, phenylthioethyl, phenylthiopropyl, etc.) esters, phenysulfenyl(lower)alkyl (e.g., phenylsulfenylmethyl, phenylsulfenylethyl, etc.) esters, lower alkanoyloxy(lower)alkyl (e.g., acetoxymethyl, propionyloxymethyl, pivaloyloxymethyl, etc.) esters, benzoyl(lower)alkyl (e.g., benzoylmethyl, etc.) esters, phthalimido ester, etc;

suitable esters containing an heterocyclic ring include, for example, heterocyclic esters, heterocyclic lower alkyl esters, etc.;

suitable heterocyclic esters include, for example, saturated or unsaturated, condensed or uncondensed 3 to 8-membered heterocyclic containing 1 to 4 hetero-atom(s) such as an oxygen, sulfur and nitrogen atom (e.g., pyridyl, piperidino, 2-pyridon-1-yl, tetrahydropyranyl, quinolyl, pyrazolyl, etc.) esters, etc.;

suitable heterocyclic lower alkyl esters include, for example, saturated or unsaturated, condensed or uncondensed 3 to 8-membered heterocyclic containing 1 to 4 hetero-atom(s) such as an oxygen, sulfur and nitrogen atom(e.g., pyridyl, piperidino, 2-pyridon-1yl, tetrahydrophyranyl, quinolyl, pyrazolyl, etc.) substituted lower alkyl(e.g., methyl, ethyl, propyl, etc.) esters, etc.;

the silyl esters, the aliphatic esters and the esters containing an aromatic or heterocyclic ring may have 1 to 10 appropriate substituent(s) such as lower alkyl (e.g., methyl, ethyl, propyl, isopropyl, butyl, tertiarybutyl, etc.), lower alkoxy(e.g., methoxy, ethoxy, propoxy, isopropoxy, butoxy, tertiarybutoxy, etc.), lower alkylthio (e.g., methylthio, ethylthio, propylthio, etc.), lower alkylsulfinyl (e.g., methylsulfinyl, ethylsulfinyl, propylsulfinyl, etc.), lower alkanesulfonyl (e.g., methanesulfonyl, ethanesulfonyl, etc.), phenylazo, halogen (e.g., chlorine, bromine, fluorine, etc.), cyano, hydroxy or nitro, for example, mono(or di or tri)-halo(lower)alkyl-(e.g., chloromethyl, bromoethyl, dichloromethyl, 2,2,2-trichloroethyl, 2,2,2-tribromoethyl, etc.) esters, cyano(-lower)alkyl(e.g., cyanomethyl, cyanoethyl, etc.) esters, mono(or di or tri or tetra or penta)halophenyl(e.g., 4-chlorophenyl, 3,5-dibromophenyl, 2,4,5-trichlorophenyl, 2,4,6-trichlorophenyl pentachlorophenyl, etc.) esters, lower alkanesulfonylphenyl(e.g., 4-methanesulfonylphenyl, 2-ethanesulfonylphenyl, etc.) esters, 2-(or 3- or 4-)phenylazophenyl esters, mono(or di or tri)nitrophenyl(e.g., 4-nitrophenyl, 2,4-dinitrophenyl, 3,4,5-trinitrophenyl, etc.) esters, mono(or di or tri or tetra or penta)halophenyl(lower)alkyl(e.g., 2-chlorobenzyl, 2,4-dibromobenzyl, 3,4,5-trichlorobenzyl, pentachlorobenzyl, etc.) esters, mono(or di or tri)nitrophenyl(lower)alkyl (e.g., 2-nitrobenzyl, 2,4-dinitrobenzyl, 3,4,5-trinitrobenzyl, etc.) esters, mono(or di or tri)-(lower)alkoxypenyl(lower)alkyl(e.g., 2-methoxybenzyl, 3,4-dimethoxybenzyl, 3,4,5-trimethoxybenzyl, etc.) esters, hydroxy and di(lower)-alkylpenyl(lower)alkyl(e.g., 3,5-dimethyl-4-hydroxybenzyl, 3,5-ditertiarybutyl-4-hydroxybenzyl, etc.) esters, etc.;

suitable acid amides include, for example, N-lower alkyl acid amide(e.g., N-methyl acid amide, N-ethyl acid amide, etc.), N,N-di(lower)alkyl acid amide(e.g., N,N-dimethyl acid amide, N,N-diethyl acid amide, N-methyl-N-ethyl acid amide, etc.), N-phenyl acid amide, or an acid amide with pyrazole, imidazole, 4-lower alkylimidazole(e.g., 4-methylimidazole, 4-ethylimidazole, etc.), etc.; suitable acid anhydrides include, for example, an acid anhydride with a di(lower)alkyl phosphate(e.g., dimethyl phosphate, diethyl phosphate, etc.), dibenzylphosphate, phosphoric acid halide(e.g., phosphoric acid chloride, phosphoric acid bromide, etc.), di(lower)alkyl phosphite (e.g., dimethyl phosphite, diethyl phosphite, etc.), sulfurous acid, thiosulfuric acid, sulfuric acid, lower alkyl carbonate (e.g., methyl carbonate, ethyl carbonate, etc.), hydrazoic acid, hydrohalogenic acid (e.g., hydrochloric acid, hydrobromic acid, etc.), lower alkanoic acid (e.g., pivalic acid, pentanoic acid, isopentanoic acid, 2-ethylbutanoic acid, valeric acid, propionic acid, etc.), lower alkenoic acid (e.g., crotonic acid, etc.), halo (lower)alkanoic acid (e.g., chloroacetic acid, etc.), halo(lower)alkenoic acid (e.g., 3-chloro-2-pentenoic acid, 3-bromo-2-butenoic acid, etc.), phenyl(lower)alkanoic acid (e.g., phenylacetic acid, etc.), phenoxy(lower)alkanoic acid (e.g., phenoxyacetic acid, etc.), furanacetic acid, thiopheneacetic acid, benzoic acid, or a symmetric acid anhydride, etc.; and suitable acid salt include an acid salt with a metal such as alkali metal (e.g., sodium, potassium, etc.) or alkaline earth metal(e.g., magnesium, etc.), or with an organic amine such as lower alkylamine, di(lower)alkylamine, tri(lower)alkylamine, aniline, pyridine, picoline, N,N'-bis[phenyl(lower)alkyl]-(lower)alkylenediamine (e.g., N,N'-dibenzylethylenediamine, etc.), or the like.;

the term "lower alkyl" for $R^3$ means the one having straight, branched or cyclic 1 6 carbon chain such as methyl, ethyl propyl, isopropyl, butyl, tert-butyl, cyclohexyl, etc.

the term "a residue of a thiol compount HX" for X means a residue given by omitting the hydrogen atom from a thiol compound HX;

suitable residues of thiol compounds include a substituted or unsubstituted, aliphatic thiol, aromatic thiol, or heterocyclic thiol compound;

suitable aliphatic thio groups include, for example, lower alkylthio(e.g., methythio, ethylthio, propylthio, isopropylthio, butylthio, isobutylthio, etc.), lower alkenylthio(e.g., vinylthio, 1-isopropenylthio, 3-butenylthio, etc.), etc.;

suitable substituted aliphatic thio groups include, for example, lower alkoxy(lower)alkylthio(e.g., methoxymethylthio, ethoxymethylthio, etc.), phenyl(lower)alkylthio(e.g., benzylthio, phenethylthio, etc.), xylyl(lower)alkylthio(e.g, xylylmethylthio, etc.), halophenyl(lower)alkylthio(e.g., 4-chlorobenzylthio, 4-brombenzylthio,etc.), nitrophenyl(lower)alkylthio (e.g., 4-nitrobenzylthio, etc.), mono(or di)lower alkoxyphenyl(lower)alkylthio(e.g., 4-methoxybenzylthio, 2,4-dimethoxybenzylthio, etc.), halogen and lower alkoxy substituted phenyl(lower)alkylthio(e.g., 2-chloro-4-methoxybenzylthio, etc.), etc.;

suitable aromatic thio groups include arylthio(e.g., phenylthio, xylylthio, tolylthio, naphthylthio, etc.), suitable substituted aromatic thio groups include, for example, mono(or di)halophenylthio(e.g., chlorophenylthio, bromophenylthio, dichlorophenylthio, etc.), nitrophenylthio, mono(or di)-lower alkoxypenylthio(e.g., methoxyphenylthio, dimethoxyphenylthio, etc.), halogen and nitro substituted phenylthio(e.g., chloronitrophenylthio, etc.), etc; suitable heterocyclic groups in the heterocyclic thio groups may contain at least one hetero-atom such as an oxygen, nitrogen, sulfur atom and the like.;

suitable heterocyclic groups include, for example, unsaturated 3to 8-membered heteromonocyclic containing a sulfur atom(e.g., thienyl, etc.), unsaturated 3 to 8-membered heteromonocyclic containing an oxygen atom (e.g., furyl, etc.), unsaturated 3 to 8-membered heteromonocyclic containing 1 to 4 nitrogen atom(s) (e.g., pyrrolyl, pyridyl, imidazolyl, triazolyl, tetrazolyl, etc.), saturated 3 to 8-membered heteromonocyclic containing 1 to 2 nitrogen atom(s)(e.g., pyrrolidinyl, piperazinyl, piperioinyl, homopiperazinyl, etc.), unsaturated condensed-heterocyclic containing 1 to 3 nitrogen atom(s) (e.g., quinolyl, isoquinolyl, benzimidazolyl, etc.), unsaturated 3 to 8-membered heteromonocyclic containing an oxygen atom and 1 to 3 nitrogen atom(s)-(e.g., oxazolyl, oxadiazolyl, oxatriazol, etc.), unsaturated 3 to 8-membered heteromonocyclic containing a sulfur and 1 to 3 nitrogen atom(s)(e.g., thiazolyl, thiadiazolyl, thiatriazolyl, etc.), unsaturated condensed-heterocyclic containing an oxygen and nitrogen atom-(e.g., benzoxazolyl, etc.), unsaturated condensed-heterocyclic containing a sulfur and nitrogen atom (e.g., benzothiazolyl, etc.); and suitable substituted heterocyclic groups in the substituted heterocyclic thio groups include, for example, the above mentioned heterocyclic groups are substituted with 1 to 6 appropriate substituent(s) such as lower alkyl radical (e.g., methyl, ethyl, etc.), a lower alkoxy radical (e.g., methoxy, ethoxy, etc.), a halogen atom (e.g., fluorine, chlorine, bromine, etc.), a nitro radical, an aryl radical (e.g., phenyl, tolyl, xylyl, etc.), halophenyl radical (e.g., chlorophenyl, etc.), nitrophenyl, a phenyl(lower)alkyl radical (e.g., benzyl, phenethyl, etc.) or the like: and the term "a residue of an amine" for Y and "a residue of an aliphatic amine" for Y' means a residue given by omitting one hydrogen atom from the amine used as a reagent in the process (B); and the term "a residue of an amine" for Y includes a residue of primary amine (e.g., a residue of primary aliphatic amine, a residue of primary aromatic amines, etc.) or a residue of secondary amine (e.g., a residue of secondary aliphatic amine, a residue of secondary aromatic amine, a residue of secondary cyclic amine, etc.);

suitable residues of primary aliphatic amine include, for example, lower alkylamino(e.g., methylamino, ethylamino, propylamino, isopropylamino, butylamino, etc.), lower or higher cycloalkylamino(e.g., cyclopentylamino, cyclohexyamino, etc.), etc.;

suitable residue of primary aromatic amine include, for example, arylamino(e.g., anilino, etc.), phenyl(lower)alkylamino (e.g., benzylamino, phenethylamino, etc.), etc.;

suitable residue of secondary aliphatic amine include, for example, di(lower)alkylamino(e.g., dimenthylamino, methylethylamino, diethylamino, dipropylamino, dibutylamino, etc.), etc.;

suitable residue of secondary aromatic amine include, for example, diarylamino(e.g., diphenylamino, etc.), bis[phenyl(lower)alkylamino (e.g., dibenzylamino, diphenethylamino, etc.), etc.]; and suitable residue of secondary cyclocyclic amine include, for example, 1-pyrrolidinyl, 1-piperidyl, morpholino, 4-(lower)alkylpiperazin-1-yl (e.g., 4-methylpiperazin-1-yl, etc.); the term "a residue of an aliphatic amine" for Y' includes a residue of primary and secondary aliphatic amines as illustrated above.

In the above and subsequent description, the term "lower" and "higher" mean respectively one to six and seven to sixteen carbon chain which may be branched or may contain a cyclic ring.

The process A of this invention comprises subjecting the compounds (II) to ring closure reaction in the presence of a condensing agent or a polar solvent to give the compounds (I). The condensing agent used for this purpose includes, for example, an organic acid such as lower alkanoic acid(e.g., acetic acid, propionic acid, etc.), lower alkanesulfonic acid(e.g., methanesulfonic acid, etc.), benzenesulfonic acid, toluenesulfonic acid, benzoic acid, or the like, an inorganic acid such as hydrohalogenic acid(e.g., hydrocholoric acid, hydrobromic acid, hydrofluoric acid, etc.), hydrazoic acid, carbonic acid, sulfuric acid, phosphoric acid, nitric acid, hydrocyanic acid, perchloric acid, etc., an acid catalyst (e.g., boron trifluoride, etc.), a metal salt of above recited acid wherein said metal may be alkali metal (e.g., lithium, sodium, potassium, etc.), alkaline earth metal (e.g., magnesium, etc.), silver, copper, mercury, etc., mercury oxide, cuprous oxide, methyl iodide, etc, an organic salt of the above recited acid wherein said organic amine may be mono(or di or tri)-(lower)alkylamine(e.g., methylamine, dimethylamine, diethylamine, trimethylamine, triethylamine, etc.), aniline, toluidine, mono(or di)-(lower)alkylaniline(e.g., methylaniline, diethylaniline, etc.), pyridine, picoline, etc., and a base such as alkali metal hydroxide (e.g., sodium hydroxide, etc.), alkaline earth metal hydroxide (e.g., magnesium hydroxide, (etc,), alkali metal lower alkoxide (e.g., sodium methoxide, potassium ethoxide, potassium tert.-butoxide, etc.), alkaline earth metal lower alkoxide (e.g., magnessium propoxide, etc.), mono(or di or tri)-(lower)alkylamine (e.g., methylamine, dimethylamine, triethylamine, etc.), aniline, mono(or di)-(lower)alkylaniline, pyridine, picoline, 1,5-diazabicyclo[4,3,0]-non-5-ene, 1,4-diazabicyclo[2,2,2]octane, 1,8-diazabicyclo[5,4,0]-undecene-7, a basic resin (e.g., Amberlite IR-45 prepared by Rohm & Haas Co., etc.), and the like. In this reaction, the above mentioned salt of an acid can be used as a buffer solution.

In case that the buffer solution or the base in liquid is used as a base, the reaction may be carried out in a solvent such as dimethylformamide, acetone, dichloromethane, chloroform, dimethylacetamide, diethyl carbonate, acetonitrile or dioxane, and any other solvent which does not cause bad influence to this reaction. In case that the buffer solution or the base in liquid is employed as a base, the reaction may be conducted without solvent. The reaction temperature may vary over a wide range and the reaction is usually carried out at room temperature.

The reaction may be carried out in a polar solvent such as formamide, dimethylformamide, dimethylacetamide, hexamethylphosphoric triamide, water, lower alkanol (e.g., methanol, ethanol, propanol, etc.), dimethylsulfoxide, or the like, at room temperature or while being heated.

The object compounds (I) is also prepared by the process (B) which comprises reacting the compound (II) with ammonia or an amine in the presence of a removing agent of a thiol compound HX and the process (C) which comprises subjecting the resultant of the process (B) to ring closure reaction in the presence of a condensing agent.

The amine to be used in the process (B) includes all of primary and secondary amines exemplified by a substituted or unsubstituted aliphatic amine, substituted or unsubstituted aromatic amine, etc., that is primary amine (e.g., primary aliphatic amine, primary aromatic amine, etc.) or secondary amine (e.g., secondary aliphatic amine, secondary aromatic amine, secondary cyclic amine, etc.);

suitable primary aliphatic amine include, for example, lower alkylamines (e.g., methylamine, ethylamine, propylamine, isopropylamine, butylamine, etc.), lower or higher cycloalkylamines (e.g., cyclopentylamine, cyclohexyamines, etc.), etc.;

suitable primary aromatic amine includes, for example, arylamine (e.g., aniline, etc.), phenyl(lower)alkylamine (e.g., benzylamine, phenethylamine, etc.), etc.;

suitable secondary aliphatic amine includes, for example, di(lower)alkylamines (e.g. dimethylamine, methylethylamine, diethylamine, dipropylamine, dibutylamine, etc.), etc.; suitable secondary aromatic amines include, for example, diarylamines (e.g., diphenylamine, etc.), bis[phenyl(lower)alkyl]amines (e.g., dibenzylamine, diphenethylamine, etc.); and suitable secondary cyclic amines include, for example, pyrrolidine, piperidine, morpholine, 4-(lower)alkylpiperazine (e.g., 4-methylpiperazine, etc.), etc.

The removing agent of a thiol compound HX is applied in the process (B) for removing the resultant thiol compound HX given by attack of ammonia or the amine to the compounds (II).

The removing agent of a thiol compound HX to be used in the process (B) includes metallic compounds such as silver acetate, mercury acetate, copper acetate, mercurous chloride, mercuric chloride, silver chloride, mercurous nitrate, mercuric nitrate and the like. The reaction of the process (B) may be usually carried out in a solvent such as ethyl acetate, dimethylformamide, benzene, toluene, dichloromethane, chloroform and any other inert solvent may be employed. In case of that the amine in liquid is used, the reaction may be conducted without a solvent. The reaction temperature may vary over a wide range and can be selected depending to the starting compounds (II) or ammonia or the amines or the removing agents of the thiol compound HX to be used practically.

During the reaction of the process (B), the carboxy or protected carboxy for $R^2$ may be converted respectively to the protected carboxy or free carboxy. These conversions are also included in the scope of this invention.

Among the compounds (III) prepared according to the process (B), novel compounds represented by the formula (III) as mentioned before are included.

The resultant compounds (III) may be employed with or without isolation and purification from the reaction mixture for subsequent process (C).

The process (C) may be carried out in the presence of the condensing agent and solvent as same as the ones in the process (A) which is described above. Reaction temperature of the process (C) is not particularly critical and the reaction is usually conducted at room temperature.

During the reactions of the processes (A), (B) or (C), there may be produced a by-product which is given by rearrangement of the group of the formula:

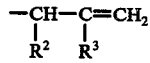

in the starting compounds (II) or the intermediates (III) to a group of the formula:

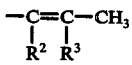

The object compounds (I) can be easily separated by the removing the by-product in the process (A) and (C) according to conventional methods.

Having now generally described the invention, a further understanding can be attained by reference to certain specific examples which are provided herein for purposes of illustration only and are not intended to be construed as limiting unless otherwise so indicated.

EXAMPLE I (1) A solution of 2,2,2-trichloroethyl 2-oxo-3-(2-phenylacetamido)-4-(benzothiazol-2-yl)dithio-α-isopropenyl-1-azetidineacetate 0.63 g and p-toluenesulfonic acid monohydrate 0.19 g in dimethylformamide 15 ml was stirred for 4.5 hours at 110° C. After completion of the reaction, the reaction mixture was poured into ice-water and extracted twice with ethyl acetate. The ethyl acetate layer was washed with water and dried over magnesium sulfate. The solvent was removed by distillation. The resulting substance 0.65 g. was subjected to silica gel chromatophraphy using chloroform to give 2,2,2-trichloroethyl 3-methyl-7-(2-phenylacetamido)-3-cephem-4-carboxylate 0.19 g having M.P. 162° C.

(2) Sodium azide 0.065 g. and water 4 ml were added to a solution of 2,2,2-trichloroethyl 2-oxo-3-(2-phenylacetamido)-4-(benzothiazol-2-yl)dithio-α-isolpropenyl-1-azetidineacetate 1.26 g in acetone 15 ml, and the mixture was stirred for 2.5 hours. The reaction mixture was filtered, and then the acetone was removed by distillation under reduced pressure. The aqueous layer was extracted with ethyl acetate and dried over magnesium sulfate. The resulting substance 1.2 g was subjected to silica gel column chromatoghraphy using chloroform to give 2,2,2-trichloroethyl 3-methyl-7-(2-phenylacetamido)-3-cephem-4-carboxylate 0.28 g having M.P. 162° C. The same results were given by using sodium hydrogen carbonate, potassium cyanide or a weak basic resin (IR-4₅) instead of sodium azide in the Example 2.

(3) Pyridine hydrobromide 0.08 g was added to a solution of 2,2,2-trichloroethyl 2-oxo-3-(2-phenylacetamio)4-(benzothiazol-2-yl)dithio-α-isopropenyl-1-azetidineacetate 1.26 g in dichloroethane 15 ml. and the mixture was stirred for 2 hours at 50° C and refluxed for 5 hours. The reaction mixture was washed with water and dried over magnesium sulfate. The solvent was removed by distillation. The resulting substance was subjected to silica gel column chromatography using chloroform to give 2,2,2-trichloroethyl 3-methyl-7-(2-phenylacetamido)-3-cephem-4-carboxylate having M.P. 162° C.

(4) Pyridine hydrobromide 0.08 g was added to a solution of methyl 2-oxo-3-(2-phenoxyacetamido)-4-(benzothiazol-2-yl)dithio-α-isopropenyl-1-azetidineacetate 1.06 g in dichloroethane 15 ml. and the mixture was refluxed for 12 hours. The reaction mixture was washed with water and dried over magnesium sulfate. The solvent was removed by distillation. The resulting substance was subjected to silica gel column chromatoghraphy to give methyl 3-methyl-7-(2-phenoxyacetamido)-3-cephem-4-carboxylate having M.P. 124° C.

(5) Acetic acid 5 ml was added to a solution of 2,2,2-trichloroethyl 2-oxo-3-(2-phenylacetamido)-4-(benzothiazol-2-yl)dithio-α-isopropenyl-1-azetidineacetate 1.26 g in ethyl acetate 15 ml and then to the mixture was added silver acetate 0.68 g at room temperature under stirring, and the reaction mixture was stirred for 4 hours at the same temperature. After completion of the reaction, the reaction mixture was filterred. The filtrate was washed with water and with 5% sodium hydrogen carbonate in turn, and filtered again. The resultant filtrate was washed with water and dried. The solvent was removed by distillation. The resulting oily substance was refined by thin layer chromatography using a mixture solvent of acetone and benzene (1:9) to give colourless needless of 2,2,2-trichloroethyl 3-methyl-7-(2-phenylacetamido)-3-cephem-4-carboxylate having M.P. 161° to 162° C.

(6) Silver fluoride 0.252 g was added to a solution of 2,2,2-trichloroethyl 2-oxo-3-(2-phenylacetamido)-4-(benzothiazol-2-yl)dithio-α-isopropenyl-1-azetidineacetate 0.63 g in acetonitrile 20 ml at room temperature under stirring and the reaction mixture was stirred for 4 hours at the same temperature. After filtration of the reaction mixture, the filtrate was concentrated. The resulting substance was extracted with ethyl acetate. The extract was washed with 5% phosphoric acid and water in turn, dried and then concentrated. The resulting substance was crystallized from ehtyl ether to give 2,2,2-trichloroethyl 3-methyl-7-(2-phenyl-acetamido)-3-cephem-4-carboxylate 0.41 g having M.P. 161° to 162° C.

(7) A solution of methyl 2-oxo-3-(2-phenoxyacetamido)-4-(benzothiazol-2-yl)dithio-α-isopropenyl-1-azetidineacetate 0.53 g and dimethylamine hydrochloride 0.07 g in N,N-dimethylacetamide 25 ml was stirred for 3.5 hours at 130° C under heating. After completion of the reaction, the reaction mixture was poured into ice-water 150 ml and then extracted with ethyl acetate. The extract was washed with water, dried and then concentrated. The resulting oily substance was refined by column chromatoghraphy on silica gel 20 g to give methyl 3-methyl-7-(2-phenoxyacetamido)-3-cephem-4-carboxylate having M.P. 124° to 125° C.

Infrared Absorption Spectrum (Nujol): 3250, 1773, 1725, 1660 cm⁻¹

Nuclear Magnetic Resonance Spectrum (CDCl₃, τ)

| 7.84 | (S, 3H) |
|---|---|
| 6.73, 6.44 | (aBq, 2H, J=18 Hz) |
| 6.15 | (S, 3H) |
| 5.42 | (S, 2H) |
| 5.00 | (d, 1H, J=5 Hz) |
| 4.18 | (q, 1H, J=5 and 9 Hz) |
| 2.5 to 3.2 | (m, 6H) |

(8) Methyl iodide 0.54 g was added to a solution of 2,2,2-trichloroethyl 2-oxo-3-(2-phenylacetamido)-4-(benzothiazol-2-yl)dithio-α-isopropenyl-1-azetidineacetate 0.64 g in dichloroethane 20 ml. The mixture was placed in a sealed tube and then heated for 24 hours at 60° C. After completion of the reaction, the reaction mixture was concentrated. The resulting oily substance was subjected to chromatoghraphy on silica gel 25 g using chloroform. The eluate was concentrated to give crystals 60 mg of 2,2,2-trichloroethyl 3-methyl-7-(2-phenylacetamido)-3-cephem-4-carboxylate having M.P. 161° to 162° C.

(9) A solution of 2,2,2-trichloroethyl 2-oxo-3-(2-phenylacetamido)-4-(benzothiazol-2-yl)dithio-α-isopropenyl-1-azetidineacetate 0.64 g in dimethylformamide 10 ml was allowed to stand for 72 hours at room temperature.

After completion of the reaction, the reaction mixture was poured into water 100 ml and then was extracted with ethyl acetate. The extract was washed and dried. The solvent was removed by distillation. The resulting oily substance was refined by column chromatography on silica gel 20 g using chloroform to give crystals 160 mg of 2,2,2-trichloroethyl 3-methyl-7-(2-phenylacetamido)-3-cephem-4-carboxylate having M.P. 161° to 162° C.

(10) A solution of 2,2,2-trichloroethyl 2-oxo-3-(2-phenylacetamido)-4-(benzothiazol-2-yl)dithio-α-isopropenyl-1-azetidineacetate 0.63 g in dimethyl sulfoxide 20 ml was heated for 6 hours at 60° C. After completion of the reaction, the reaction mixture was poured into water 150 ml and then extracted with ethyl acetate. The extract was washed with water and dried. The solvent was distilled off. The resulting oily substance was refined by column chromatoghraphy on silica gel 25 g using chloroform to give crystals 190 mg of 2,2,2-trichloroethyl 3-methyl-7-(2-phenylacetamido)-3-cephem-4-carboxylate having M.P. 161° to 162° C.

The following compounds were obtained by using substantially the same procedures as those of the Examples I — (1) to (10).

(11) 3-methyl-7-(2-phenoxyacetamido)-3-cephem-4-carboxylic acid (M.P. 172° to 175° C)

(12) 2,2,2-trichloroethyl 3-methyl-7-[N-(2,2,2-trichloroethoxy)carbonylphenylglycyl]amino-3-cephem-4-carboxylate (M.P. 99° to 100.5° C)

(13) 2,2,2-trichloroethyl 3-methyl-7-(2-phenoxyacetamido)-3-cephem-4-carboxylate (M.P. 111° to 113° C)

(14) 1-cyclopropylethyl 3-methyl-7-(2-phenylacetamido)-3-cephem-4-carboxylate (M.P. 108° to 112° C)

(15) 2,2,2-trichloroethyl 3-methyl-7-[2-(sydnon-3-yl)acetamido]-3-cephem-4-carboxylate [M.P. 116 to 119° C (dec.)]

(16) 2,2,2-trichloroethyl 3-methyl-7-[2-(p-hydroxyphenyl)-2-(1-cyclopropylethoxy)carbonylaminoacetamido]-3-cephem-4-carboxylate [Infrared Absorption Spectrum (Liquid film) : 3300, 1775, 1740, 1675 cm$^{-1}$]

(17) 2,2,2-trichloroethyl 3-methyl-7-[2-(2-thienyl)acetamido]-3-cephem-4-carboxylate (M.P. 151° to 152° C)

(18) 3,5-ditertiarybutyl-4-hydroxybenzyl 3-methyl-7-(2-phenylacetamido)-3-cephem-4-carboxylate

[Infrared Absorption Spectrum : 1780, 1730, 1665 cm$^{-1}$]

(19) 2,2,2-trichloroethyl 3-methyl-7-[N-(1-cyclopropylethoxy)carbonylphenylglycyl]amino-3-cephem-4-carboxylate (M.P. 130° to 135° C)

(20) 2,2,2-trichloroethyl 3-methyl-7-(2-cyanoacetamido)-3-chephem-4-carboxylate [M.P. 154° to 159° C (dec.)]

EXAMPLE II (1)-(i) Ethyl acetate 15 ml was added to a solution of methyl 2-oxo-3-(2-phenoxyacetamido)-4-(benzothiazol-2-yl)-dithio-α-isopropenyl-1-azetidineacetate 0.59 g in dichloromethane and to which were added n-propylamine 0.06 g and silver acetate in turn at $-10°$ to $-15°$ C, and then the reaction mixture was stirred for 4 hours at the same temperature. After completion of the reaction, the reaction mixture was filtered. The filtrate was washed with 5% phosphoric acid and water in turn. The filtrate was dried and then the solvent was removed by distillation to give oily methyl 2-oxo-3-(2-phenoxyacetamido)-4-propylaminothio-α-isopropenyl-1-azetidineacetate 0.452 g.

Infrared absorption spectrum: 3300, 1770, 1740, 1685 cm$^{-1}$

Nuclear Magnetic Resonance Spectrum (CDCl$_3$, τ)

| | |
|---|---|
| 9.18 | (t, 3H, J=6 Hz) |
| 8.67 | (m, 2H) |
| 8.10 | (s, 3H) |
| 7.23 | (t, 2H, J=7 Hz) |
| 6.05 | (s, 3H) |
| 5.43 | (s, 2H) |
| 5.24 | (s, 1H) |
| 5.04 | (d, 1H, J=5 Hz) |
| 4.90 | (m, 2H) |
| 4.30 | (q, 1H, J=5 and 9 Hz) |
| 2.65 to 3.22 | (m, 5H) |
| 2.27 | (d, 1H, J=9 Hz) |

(1)-(ii) Boron trifluoride ethyl etherate 0.08 g was added to a solution of methyl 2-oxo-3-(2-phenoxyacetamido)-4-propylaminothio-α-isopropenyl-1-azetidineacetate 0.452 g in dried dichloromethane 20 ml under ice-cooling, and the mixture was stirred for 6 hours at the same temperature. After completion of the reaction, the reaction mixture was washed with 5% sodium hydrogen carbonate aqueous solution and water in turn. The reaction mixture was dried and then the solvent was distilled off. The resulting oily substance was subjected to column chromatography on silica gel 11 g and eluted with chloroform.

An oily substance was given from the 4th to 5th fraction (each fraction is 50 ml). This substance was treated with ether and resulting precipitates were collected by filtration and dried to give colorless crystals of methyl 3-methyl-7-(2-phenoxyacetamido)-3-cephem-4-carboxylate having M.P. 124° to 125° C.

Infrared Absorption Spectrum (Nujol): 3250, 1773, 1725, 1660 cm$^{-1}$

Nuclear Magnetic Resonance Spectrum (CDCl$_3$, τ)

| | |
|---|---|
| 7.84 | (s, 3H) |
| 6.73 to 6.44 | (ABq, 2H, J=18 Hz) |
| 6.15 | (s, 3H) |
| 5.42 | (s, 2H) |
| 5.00 | (d, 1H, J=5 Hz) |
| 4.18 | (q, 1H, J=5 and 9 Hz) |
| 2.5 to 3.2 | (m, 6H) |

The following compounds were obtained by using substantially the same procedure as that of the Example (II)-(1) (i and ii).

(2) 3-methyl-7-(2-phenoxyacetamido)-3-cephem-4-carboxylic acid (M.P. 172° to 175° C)

(3) 2,2,2-trichloroethyl 3-methyl-7-[N-(2,2,2-trichloroethoxy)carbonylphenylglycyl]amino-3-cephem-4-carboxylate (M.P. 99° to 100.5° C)

(4) 2,2,2-trichloroethyl 3-methyl-7-(2-phenoxyacetamido)-3-cephem-4-carboxylate (M.P. 111° to 113° C)

(5) 1-cyclopropylethyl 3-methyl-7-(2-phenylacetamido)-3-cephem-4-carboxylate (M.P. 108° to 112° C)

(6) 2,2,2-trichloroethyl 3-methyl-7-[2-(syndon-3-yl)acetamido]-3-cephem-4-carboxylate [M.P. 116° to 119° C (dec.)]

(7) 2,2,2-trichloroethyl 3-methyl-7-[2-(p-hydroxyphenyl)-2-(1-cyclopropylethoxy)carbonylaminoacetamido]-3-cephem-4-carboxylate

[Infrared Absorption Spectrum (Liquid film): 3300, 1775, 1740, 1675 cm$^{-1}$]

(8) 2,2,2-trichloroethyl 3-methyl-7-[2-(2-thienyl)acetamido]-3-cephem-4-carboxylate (M.P. 151° to 152° C)

(9) 3,5-ditertiarybutyl-4-hydroxybenzyl 3-methyl-7-(2-phenylacetamido)-3-cephem-4-carboxylate [Infrared Absorption Spectrum: 1780, 1730, 1665 cm$^{-1}$]

(10) 2,2,2-trichloroethyl 3-methyl-7-[N-(1-cyclopropylethoxy)carbonylphenylglycyl]amino-3-cephem-4-carboxylate (M.P. 130° to 135° C)

(11) 2,2,2-trichloroethyl 3-methyl-7-(2-cyanoacetamido)-3-cephem-4-carboxylate [M.P. 154° to 159° C (dec.)]

(12) 2,2,2-trichloroethyl 3-methyl-7-(2-phenylacetamido)-3-cephem-4-carboxylate (M.P. 162° C)

EXAMPLE III (1) N-propylamine 0.06g was added to a solution of 1-cyclopropylethyl 2-oxo-3-(2-phenoxyacetamido)-4-(benzothiazol-2-yl)dithio-α-isopropenyl-1-azetidineacetate 0.505 g in ethyl acetate 20 ml at −10° to −15° C and to the resultant mixture was added silver acetate 0.325 g under stirring, and the reaction mixture was stirred for 5 hours at the same temperature. After completion of the reaction, the reaction mixture was filterred. The filtrate was washed with ice-water, 5% phosphoric acid and ice-water in turn. The filtrate was dried and then the solvent was removed by distillation under reduced pressure under water cooling to give yellowish brown oil 0.355 g of 1-cyclopropylethyl 2-oxo-3-(2-phenoxyacetamido)-4-propylaminothio-α-isopropenyl-1-azetidineacetate.

Infrared Absorption Spectrum (Liquid film): 3300, 1780, 1740, 1690 cm$^{-1}$

Nuclear Magnetic Resonance Spectrum (CDCl$_3$, τ)

| 8.7 to 10.0 | (m, 5H) |
| 9.18 | (t, 3H, J=6 Hz) |
| 8.65 | (d, 3H, J=6 Hz) |
| 8.67 | (m, 2H) |
| 8.05 | (s, 3H) |
| 7.22 | (t, 2H, J=7 Hz) |
| 5.42 to 5.67 | (m, 1H) |
| 5.43 | (s, 1H) |
| 5.40 | (s, 2H) |
| 5.22 | (s, 1H) |
| 4.97 | (d, 1H, J=4 Hz) |
| 4.72 to 4.93 | (m, 2H) |
| 4.28 | (q, 1H, J=4.8 Hz) |
| 2.60 to 3.15 | (m, 5H) |

(2) Piperidine 0.74 g and silver acetate 0.332 g were added to a solution of methyl 2-oxo-3-(2-phenoxyacetamido)-4-(benzothiazol-2-yl)dithio-α-isopropenyl-1-azetidineacetate 0.53 g in ethyl acetate 25 ml, and the reaction mixture was stirred for 5 hours at room temperature. After completion of the reaction, the reaction mixture was filtered. The filtrate was washed with 5% phosphoric acid and then with water several times. The filtrate was dried, and then the solvent was distilled off to give methyl 2-oxo-3-(2-phenoxyacetamido)-4-piperidinothio-α-isopropylidene-1-azetidineacetate 370 mg. This substance was dissolved in ether and placed under ice-cooling. The precipitates were collected by filtration and dried to give methyl 2-oxo-3-(2-phenoxyacetamido)-4-piperidinothio-α-isopropylidene-1-azetidineacetate having M.P. 65° C.

Analysis calculated for C$_{22}$H$_{29}$N$_3$O$_5$S (in percentage): C: 58.55; H: 6.54; N: 9.38; Found: C: 58.37; H: 6.46; N: 9.24.

Infrared Absorption Spectrum (Nujol) 3300, 1770, 1730, 1690 cm$^{-1}$

Nuclear Magnetic Resonance Spectrum (CDCl$_3$, τ)

| 8.37 to 8.77 | (m, 6H) |
| 7.95 | (s, 3H) |
| 7.72 | (s, 3H) |
| 7.00 to 7.30 | (m, 4H) |
| 6.20 | (s, 3H) |
| 5.40 | (s, 2H) |
| 4.43 to 4.57 | (m, 2H) |
| 2.50 to 3.12 | (m, 6H) |

(3) Aniline 0.8 g and silver acetate 0.34 g were added to a solution of 1-cyclopropylethyl 2-oxo-3-(2-phenoxyacetamido)-4-(benzothiazol-2-yl)dithio-α-isopropenyl-1-azetidineacetate 1.24 g in ethyl acetate 50 ml, and the mixture was stirred for 24 hours at room temperature. After completion of the reaction, the reaction mixture was filtered. The filtrate was washed with 5% phosphoric acid and then with water several times. The filtrate was dried and then the solvent was removed by distillation. The resulting oily substance was refined by silica gel column chromatography to give colourless oil 930 mg of 1-cyclopropylethyl 2-oxo-3-(2-phenoxyacetamido)-4-anilinothio-α-isopropenyl-1-azetidineacetate.

Infrared Absorption Spectrum (Liquid film): 3325, 1770, 1737, 1688 cm$^{-1}$

Nuclear Magnetic Resonance Spectrum (CDCl$_3$, τ)

| 8.80 to 10.00 | (m, 5H) |
| 8.75 | (s, 3H) |
| 8.65 | (s, 3H) |
| 8.02 | (s, 3H) |
| 5.40 to 5.85 | (m, 1H) |
| 5.48 | (s, 2H) |
| 5.30 | (s, 1H) |
| 5.20 | (s, 1H) |
| 4.87 | (d, 1H) |
| 4.8 to 4.88 | (m, 2H, J=5 Hz) |
| 5.58 | (q, 1H, J=5 and 9 Hz) |
| 2.6 to 3.33 | (m, 10H) |

(4) Aniline 0.19 g and silver acetate 0.34 g were added to a solution of 2,2,2-trichloroethyl 2-oxo-3-(2-phenylacetamido)-4-(benzothiazol-2-yl) dithio-α-isopropenyl-1-azetidineacetate 1.26 g in ethyl acetate, and the reaction mixture was stirred for 32 hours at room temperature. After completion of the reaction, the reaction mixture was filterred. The filtrate was washed with 5% phosphoric acid three times and then with water several times. The filtrate was dried and the solvent was removed by distillation. The resulting oily substance was refined by silica gel column chromatography using chloroform. Pale yellowish oil 130 mg of 2,2,2-trichloroethyl 2-oxo-3-(2-phenylacetamido)-4-anilinothio-α-isopropenyl-1-azetidineacetate was given from 5th to 6th fractions (each fraction is 50 ml).

Infrared Absorption Spectrum (Chloroform): 3400, 1770, 1745, 1675 cm$^{-1}$

Nuclear Magnetic Resonance Spectrum (CDCl$_3$, τ)

| | |
|---|---|
| 8.13 | (s, 3H) |
| 6.55 | (s, 2H) |
| 5.17 | (q, 2H, J=4 Hz) |
| 5.00 | (s, 1H) |
| 4.82 | (d, 1H, J=4 Hz) |
| 4.75 to 4.87 | (m, 2H) |
| 4.47 | (q, 1H, J=4 and 8 Hz) |
| 2.70 to 3.15 | (m, 10 H) |

2,2,2-trichloroethyl 2-oxo-3-(2-phenylacetamido)-4-anilinothio-α-isopropylidene-1-azetidineacetate 610 mg was given from the above 8th to 10th fractions.

Infrared Absorption Spectrum (Nujol): 3400, 1770, 1725, 1680 cm$^{-1}$

Nuclear Magnetic Resonance Spectrum (CDCl$_3$, τ)

| | |
|---|---|
| 7.97 | (s, 3H) |
| 7.70 | (s, 3H) |
| 6.37 | (s, 2H) |
| 5.37 | (q, 2H, J=12 Hz) |
| 5.13 | (s, 1H) |
| 4.70 to 4.83 | (m, 2H) |
| 2.68 to 3.33 | (m, 10 H) |

(5) Aniline (0.745 g) and silver acetate (0.332 g) were added to a solution of methyl 2-oxo-3-(2-phenoxyacetamido)-4-(benzothiazol-2-yl)dithio-α-isopropenyl-1-azetidineacetate 0.53 g in ethyl acetate 30 ml, and the mixture was stirred for 19 hours at room temperature. After completion of the reaction, the reaction mixture was filtered. The filrate was washed with 5% phosphoric acid twice or three times and with water several times. The filtrate was dried and then the solvent was removed by distillation. The resulting oily substance was refined by silica gel column chromatography using chloroform to give colorless oil 0.395 g methyl 2-oxo-3-(2-phenoxyacetamido)-4-anilinothio-α-isopropenyl-1-azetidineacetate.

Infrared Absorption Spectrum (Liquid film): 3325, 1770, 1746, 1680 cm$^{-1}$

Nuclear Magnetic Resonance Spectrum (CDCl$_3$, τ)

| | |
|---|---|
| 8.05 | (s, 3H) |
| 6.27 | (s, 3H) |
| 5.47 | (s, 2H) |
| 5.27 | (s, 1H) |
| 5.22 | (s, 1H) |
| 4.77 to 4.95 | (m, 2H) |
| 4.92 | (d, 1H, J=5 Hz) |
| 4.58 | (q, 1H, J=5 and 8 Hz) |
| 2.54 to 3.25 | (m, 10H) |

What is claim is:
1. A process for the preparation of the compound of a formula:

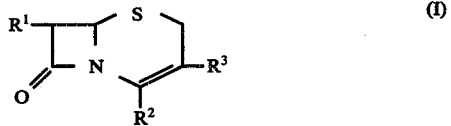

wherein
R$^1$ is substituted amino selected from the group consisting of hydrazino, mono- or di-(C$_1$-C$_6$)alkylamino, mono- or di-(C$_2$-C$_6$)alkenylamino, mono- or di-(C$_2$-C$_6$)alkylideneamino, phenyl(C$_1$-C$_6$)-alkylideneamino and acylamino wherein said acyl radical is selected from the group consisting of (C$_1$-C$_6$)alkanoyl, (C$_3$-C$_6$)alkenoyl, (C$_3$-C$_6$)alkynoyl, cyclo(C$_5$-C$_8$)alkanecarbonyl, cyclo(C$_5$-C$_8$)alkyl(C$_2$-C$_6$)alkanoyl, dihydrobenzoyl, dihydrophenyl(C$_2$-C$_6$)alkanoyl, (C$_1$-C$_6$)alkoxy(C$_2$-C$_6$)alkanoyl, (C$_1$-C$_6$)alkylthio(C$_2$-C$_6$)alkanoyl, (C$_2$-C$_6$)alkenylthio(C$_2$-C$_6$)alkanoyl, cyclo(C$_5$-C$_8$)alkylthio(C$_2$-C$_6$)alkanoyl, cyclo(C$_5$-C$_8$)alkoxy(C$_2$-C$_6$)alkanoyl, dihydrophenoxy(C$_2$-C$_6$)alkanoyl, dihydrophenylthio(C$_2$-C$_6$)alkanoyl, (C$_1$-C$_6$)alkoxycarbonyl, cyclo(C$_3$-C$_8$)alkyl(C$_1$-C$_6$)alkoxycarbonyl, cyclo(C$_5$-C$_8$)alkoxycarbonyl dihydrophenoxycarbonyl, phenylcarbamoyl, benzoyl, toluoyl, naphthoyl, α-methylnaphthoyl, benzenesulfonyl, tetrahydronaphthoyl, indancarbonyl, phenyl(C$_2$-C$_6$)alkanoyl, tolyl(C$_2$-C$_6$)alkanoyl, xylyl(C$_2$-C$_6$)alkanoyl, naphthyl(C$_2$-C$_6$)-alkanoyl, tetrahydronaphthyl(C$_2$-C$_6$)alkanoyl, indanyl(C$_2$-C$_6$)alkanoyl, phenoxy(C$_2$-C$_6$)alkanoyl, xylyloxy(C$_2$-C$_6$)alkanoyl, phenoxycarbonyl, xylyloxycarbonyl, naphthyloxycarbonyl, indanyloxycarbonyl, phenyl(C$_1$-C$_6$)alkoxycarbonyl, phenylthio(C$_2$-C$_6$)alkanoyl, phenylglyoxyloyl, heterocyclic carbonyl, heterocyclic(C$_2$-C$_6$)alkanoyl, heterocyclic (C$_1$-C$_6$)alkoxycarbonyl, heterocyclic-oxycarbonyl, heterocyclicoxy(C$_2$-C$_6$)alkanoyl, heterocyclic-thio(C$_2$-C$_6$)alkanoyl wherein said heterocyclic group is selected from the group consisting of thienyl, benzothienyl, furyl, 2- or 4-pyranyl, 5,6-dihydro-2H-pyran-3-yl), pyrrolyl, 2- or 3H-pyrrolyl, 2- or 3-pyrrolinyl, imidazolyl, pyrazolyl, pyridyl, pyrimidyl, pyrazinyl, pyridazinyl, 1H-tetrazolyl, 2H-tetrazolyl, pyrrolidinyl, imidazolidinyl, piperidino, piperazinyl, indolyl, isoindolyl, indolizinyl, benzimidazolyl, quinolyl, isoquinolyl, 1- or 2H-indazolyl, 1- or 2H-benzotriazolyl, oxazolyl, isoxazolyl, oxadiazolyl, sydnonyl, thiazolyl, thiadiazolyl, benzoxazolyl, benzoxadiazolyl, benzothiazolyl, and benzothiadiazolyl; the above recited acyl group having from 1 to 10 of the substituents selected from the group consisting of (C$_1$-C$_6$) alkyl, (C$_2$-C$_6$)alkenyl, cyclo(C$_3$-C$_8$)alkyl, (C$_1$-C$_6$)alkoxy, (C$_1$-C$_6$)alkylthio phenyl, xylyl, tolyl, indanyl, phenyl(C$_1$-C$_6$) alkyl, halogen, halophenyl, halophenoxy, cyano, (C$_1$-C$_6$)alkylsulfinyl, (C$_1$-C$_6$)alkanesulfonyl, (C$_1$-C$_6$)alkoxycarbonyl(C$_1$-C$_6$)alkoxy, cyclo(C$_3$-C$_8$)alkyl(C$_1$-C$_6$)alkoxycarbonyl(C$_1$-C$_6$)alkoxy, nitro, sulfo, amino, azido, mercapto, carboxy, hydroxy, hydroxyamino, and mono- or di-(C$_1$-C$_6$)alkylamino, said above recited acyl group having a functional group selected from the group consisting of amino, hydroxy, mercapto and carboxy, wherein said functional group is protected by a conventional protecting group;

R$^2$ is carboxy or protected carboxy, wherein said protected carboxy is an ester in which the ester moiety is selected from the group consisting of tri(C$_1$-C$_6$)alkylsilyl, (C$_1$-C$_6$)alkyl, cyclo(C$_3$-C$_8$)alkyl(C$_1$-C$_6$)alkyl, (C$_2$-C$_6$)alkenyl, (C$_2$-C$_6$)alkynyl, cyclo(C$_5$-C$_8$)alkyl, (C$_1$-C$_6$)alkoxy(C$_1$-C$_6$)alkyl, (C$_1$-C$_6$)alkylthio(C$_1$-C$_6$)alkyl, di(C$_1$-C$_6$)alkylamino, (C$_1$-C$_6$)alkylideneamino, (C$_1$-C$_6$)alkylsulfenyl(C$_1$-C$_6$)alkyl, phenyl, xylyl, tolyl, naphthyl, indanyl, dihydroanthryl, phenyl(C$_1$-C$_6$)alkyl, phenoxy(C$_1$-C$_6$)alkyl, phenylthio(C$_1$-C$_6$)alkyl, phenylsulfenyl(C$_1$-C$_6$)alkyl, (C$_1$-C$_6$)alkanoyloxy(C$_1$-C$_6$)alkyl, benzoyl(C$_1$-C$_6$)alkyl, phthalimido, pyridyl, piperidino, 2-pyridon-1-yl, tetrahydropyranyl, quinolyl, pyrazolyl, heterocyclic($C_1$-$C_6$)alkyl, wherein said heterocyclic group is selected from the group consisting of pyridyl, piperidino, 2-pyridon-1-yl, tetrahydropyranyl, quinolyl, and pyrazolyl; the above recited protected carboxy ester having 1 to 10 substituents selected from the group consisting of ($C_1$-$C_6$)alkyl, ($C_1$-$C_6$)alkoxy, ($C_1$-$C_6$)alkylthio, ($C_1$-$C_6$)alkylsulfinyl, ($C_1$-$C_6$)alkanesulfonyl, phenylazo, halogen, cyano, hydroxy, and nitro; acid amide selected from the group consisting of N-($C_1$-$C_6$)alkyl acid amide, N,N-di($C_1$-$C_6$)alkyl acid amide, N-phenyl acid amide, and acid amide with pyrazole, imidazole, 4-($C_1$-$C_6$)alkylimidazole; acid anhydride selected from the group consisting of acid anhydride of di($C_1$-$C_6$)alkyl phosphate, dibenzylphosphate, phosphoric acid halide, di($C_1$-$C_6$)alkyl phophite, sulfurous acid, thiosulfuric acid, sulfuric acid, ($C_1$-$C_6$)alkyl carbonate, hydrazoic acid, hydrohalogenic acid, ($C_1$-$C_6$)alkanoic acid, ($C_3$-$C_6$)alkenoic acid, halo($C_2$-$C_6$)alkanoic acid, halo($C_3$-$C_6$)alkenoic acid, phenyl($C_2$-$C_6$) alkanoic acid, phenoxy($C_2$-$C_6$)alkanoic acid, furanacetic acid, thiopheneacetic acid, benzoic acid, and symmetric acid anhydride;

acid salt selected from the group consisting of the alkali metal salt, alkaline earth metal salt, and a salt with an organic amine selected from the group consisting of ($C_1$-$C_6$)alkylamine, di($C_1$-$C_6$)alkylamine, tri($C_1$-$C_6$)alkylamine, aniline, pyridine, picoline, and N,N -bis[phenyl($C_1$-$C_6$)alkyl]-($C_1$-$C_6$)alkylenediamine, and $R^3$ is ($C_1$-$C_6$)alkyl, which consists essentially of: reacting a compound of the formula:

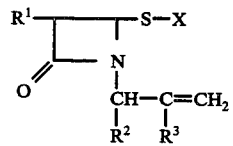

wherein $R^1$, $R^2$ and $R^3$ are each as defined above, and

X is a residue of a thiol compound selected from the group consisting of ($C_1$-$C_6$)alkylthio, ($C_2$-$C_6$)alkenylthio, ($C_1$-$C_6$)alkoxy($C_1$-$C_6$)alkylthio, phenyl($C_1$-$C_6$)alkylthio, xylyl($C_1$-$C_6$)alkylthio, halophenyl($C_1$-$C_6$)alkylthio, nitrophenyl($C_1$-$C_6$)alkylthio, mono- or di-($C_1$-$C_6$)alkoxyphenyl($C_1$-$C_6$)alkylthio, halo and ($C_1$-$C_6$)alkoxy substituted phenyl($C_1$-$C_6$)alkylthio, phenylthio, xylylthio, tolylthio, naphthylthio, mono- or di-halophenylthio, nitrophenylthio, mono- or di-($C_1$-$C_6$)alkoxyphenylthio, halo and nitro substituted phenylthio, heterocyclic thio wherein said heterocyclic group is selected from the group consisting of thienyl, furyl, pyrrolyl, pyridyl, imidazolyl, triazolyl, tetrazolyl, pyrrolidinyl, piperazinyl, piperidinyl, homopiperazinyl, quinolyl, isoquinolyl, benzimidazolyl, oxazolyl, oxadiazolyl, oxatriazolyl, thiazolyl, thiadiazolyl, thiatriazolyl, benzoxazolyl and benzothiazolyl, the above recited heterocyclic group having 1 to 6 substituents selected from the group consisting of ($C_1$-$C_6$)alkyl, ($C_1$-$C_6$)alkoxy, halogen, nitro, phenyl, tolyl, xylyl, halophenyl, nitrophenyl, and phenyl($C_1$-$C_6$)alkyl, with a condensing agent selected from the group consisting of ($C_1$-$C_6$)alkanoic acid, ($C_1$-$C_6$)alkanesulfonic acid, benzenesulfonic acid, toluenesulfonic acid, benzoic acid, hydrohalogenic acid, hydrazoic acid, carbonic acid, sulfuric acid, phosphoric acid, nitric acid, hydrocyanic acid, perchloric acid, boron trifluoride, a metal salt of the above recited acid wherein said metal is selected from the group consisting of alkali metal, alkaline earth metal, silver, copper, and mercury, mercury oxide, cuprous oxide, methyl iodide, an organic amine salt of the above recited acid wherein said organic amine is selected from the group consisting of ($C_1$-$C_6$)alkylamine, di($C_1$-$C_6$)alkylamine, tri($C_1$-$C_6$)alkylamine, aniline, toluidine, ($C_1$-$C_6$)alkylaniline, di($C_1$-$C_6$)alkylaniline, pyridine, and picoline, alkali metal hydroxide, alkali metal ($C_1$-$C_6$)alkoxide, alkaline earth metal hydroxide, alkaline earth metal ($C_1$-$C_6$)alkoxide, ($C_1$-$C_6$)alkylamine, di($C_1$-$C_6$)alkylamine, tri($C_1$-$C_6$)alkylamine, aniline, ($C_1$-$C_6$)aniline, di($C_1$-$C_6$)aniline, pyridine, picoline, 1,5-diazabicyclo[4,3,0]non-5-ene, 1,4-diazabicyclo[2,2,2]octane, 1,8-diazabicyclo[5,4,0]undecene-7, and Amberlite with (trade mark) or with a polar solvent selected from the group consisting of formamide, dimethylformamide, dimethylacetamide, hexamethylphosphoric triamide, water, ($C_1$-$C_6$)alkanol, and dimethylsulfoxide at a temperature in the range of from room temperature to that resulting from the reaction mixture being heated to effect ring closure of compound (II).

2. A process for the preparation of the compound of a formula:

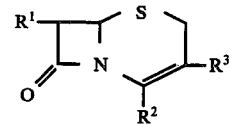

wherein $R^1$ is substituted amino selected from the group consisting of hydrazino, mono- or di-($C_1$-$C_6$)alkylamino, mono- or di-($C_2$-$C_6$)alkenylamino, mono- or di-($C_1$-$C_6$)alkylideneamino, phenyl($C_1$-$C_6$)alkylideneamino and acylamino wherein said acyl radical is selected from the group consisting of ($C_1$-$C_6$)alkanoyl, ($C_3$-$C_6$)alkenoyl, ($C_3$-$C_6$)alkynoyl, cyclo($C_5$-$C_8$)alkanecarbonyl, cyclo($C_5$-$C_8$)alkyl($C_2$-$C_6$)alkanoyl, dihydrobenzoyl, dihydrophenyl($C_2$-$C_6$)alkanoyl, ($C_1$-$C_6$)alkoxy($C_2$-$C_6$)alkanoyl, ($C_1$-$C_6$)alkylthio($C_2$-$C_6$)alkanoyl, ($C_2$-$C_6$)alkenylthio($C_2$-$C_6$)alkanoyl, cyclo($C_5$-$C_8$)alkylthio($C_2$-$C_6$)alkanoyl, cyclo($C_5$-$C_8$)alkoxy($C_2$-$C_6$)alkanoyl, dihydrophenoxy($C_2$-$C_6$)alkanoyl, dihydrophenylthio($C_2$-$C_6$)alkanoyl, ($C_1$-$C_6$)alkoxycarbonyl, cyclo($C_3$-$C_8$)alkyl($C_1$-$C_6$)alkoxycarbonyl, cyclo($C_5$-$C_8$)alkoxycarbonyl, dihydrophenoxycarbonyl, phenylcarbamoyl, benzoyl, toluoyl, naphthoyl, α-methylnaphthoyl, phthaloyl, benzenesulfonyl, tetrahydronaphthoyl, indancarbonyl, phenyl($C_2$-$C_6$)alkanoyl, tolyl($C_2$-$C_6$)alkanoyl, xylyl($C_2$-$C_6$)alkanoyl, naphthyl($C_2$-$C_6$)alkanoyl, tetrahydronaphthyl($C_2$-$C_6$)alkanoyl, indanyl($C_2$-$C_6$)alkanoyl, phenoxy($C_2$-$C_6$)alkanoyl, xylyloxy($C_2$-$C_6$)alkanoyl, phenoxycarbonyl, xylyloxycarbonyl, naphthyloxycarbonyl, indanyloxycarbonyl, phenyl($C_1$-$C_6$)alkoxycarbonyl, phenylthio($C_2$-$C_6$)alkanoyl, phenylglyoxyloyl, heterocyclic carbonyl, heterocyclic($C_2$-$C_6$)alkanoyl, heterocyclic ($C_1$-$C_6$)alkoxycarbonyl, heterocyclic-oxycarbonyl, heterocyclic-oxy($C_2$-$C_6$)alkanoyl, heterocyclic-thio($C_2$-$C_6$)alkanoyl wherein said heterocyclic group is selected from the group consisting of thienyl, benzothienyl, furyl, 2- or 4-pyranyl, 5,6-dihydro-2H-pyran-3-yl), pyrrolyl, 2- or 3H-pyrrolyl, 2- or 3-pyrrolinyl, imidazolyl, pyrazolyl, pyridyl, pyrimidyl, pyrazinyl, pyridazinyl, 1H-tetrazolyl, 2H-tetrazolyl, pyrrolidinyl, imidazolidinyl, piperidino, piperazinyl, indolyl, isoindolyl, indolizinyl, benzimidazolyl, quinolyl, isoquinolyl, 1- or 2H-indazolyl, 1- or 2H-benzotriazolyl, oxazolyl, isoxazolyl, oxadiazolyl, sydnonyl, thiazolyl, thiadiazolyl, benzoxazolyl, benzoxadiazolyl, benzothiazolyl, and benzothiadiazolyl; the above recited acyl group having from 1 to 10 of the substituents selected from the group consisting of ($C_1$-$C_6$)alkyl, ($C_2$-$C_6$)alkenyl, cyclo($C_3$-$C_8$)alkyl, ($C_1$-$C_6$)alkoxy, ($C_1$-$C_6$)alkylthio, phenyl, xylyl, tolyl, indanyl, phenyl($C_1$-$C_6$)alkyl, halogen, halophenyl, halophenoxy, cyano, ($C_1$-$C_6$)alkylsulfinyl, ($C_1$-$C_6$)alkanesulfonyl, ($C_1$-$C_6$)alkoxycarbonyl($C_1$-$C_6$)alkoxy, cyclo($C_3$-$C_8$)alkyl($C_1$-$C_6$)alkoxycarbonyl($C_1$-$C_6$)alkoxy, nitro, sulfo, amino, azido, mercapto, carboxy, hydroxy, hydroxyamino, and mono- or di-($C_1$-$C_6$)alkylamino, said above recited acyl group having a functional group selected from the group consisting of amino, hydroxy, mercapto and carboxy, wherein said functional group is protected by a conventional protecting group;

$R^2$ is carboxy or protected carboxy, wherein said protected carboxy is an ester in which the ester moiety is selected from the group consisting of tri($C_1$-$C_6$)alkylsilyl, ($C_1$-$C_6$)alkyl, cyclo($C_3$-$C_8$)alkyl($C_1$-$C_6$)alkyl, ($C_2$-$C_6$)alkenyl, ($C_2$-$C_6$)alkynyl, cyclo($C_5$-$C_8$)alkyl, ($C_1$-$C_6$)alkoxy($C_1$-$C_6$)alkyl, ($C_1$-$C_6$)alkylthio($C_1$-$C_6$)alkyl, di($C_1$-$C_6$)alkylamino, ($C_1$-$C_6$)alkylideneamino, ($C_1$-$C_6$)alkylsulfenyl($C_1$-$C_6$)alkyl, phenyl, xylyl, tolyl, naphthyl, indanyl, dihydroanthryl, phenyl($C_1$-$C_6$)alkyl, phenoxy($C_1$-$C_6$)alkyl, phenylthio($C_1$-$C_6$)alkyl, phenylsulfenyl($C_1$-$C_6$)alkyl, ($C_1$-$C_6$)alkanoyloxy($C_1$-$C_6$)alkyl, benzoyl($C_1$-$C_6$)alkyl, phthalimido, pyridyl, piperidino, 2-pyridon-1-yl, tetrahydropyranyl, quinolyl, pyrazolyl, heterocyclic($C_1$-$C_6$)alkyl, wherein said heterocyclic group is selected from the group consisting of pyridyl, piperidino, 2-pyridon-1-yl, tetrahydropyranyl, quinolyl, and pyrazolyl; the above recited protected carboxy ester having 1 to 10 substituents selected from the group consisting of ($C_1$-$C_6$)alkyl, ($C_1$-$C_6$)alkoxy, ($C_1$-$C_6$)alkylthio, ($C_1$-$C_6$)alkylsulfinyl, ($C_1$-$C_6$)alkanesulfonyl, phenylazo, halogen, cyano, hydroxy, and nitro;

acid amide selected from the group consisting of N-($C_1$-$C_6$)alkyl acid amide, N,N-di($C_1$-$C_6$)alkyl acid amide, N-phenyl acid amide, and acid amide with pyrazole, imidazole, 4-($C_1$-$C_6$)alkylimidazole;

acid anhydride selected from the group consisting of acid anhydride of di($C_1$-$C_6$)alkyl phosphate, dibenzylphosphate, phosphoric acid halide, di($C_1$-$C_6$)alkyl phophite, sulfurous acid, thiosulfuric acid, sulfuric acid, ($C_1$-$C_6$)alkyl carbonate, hydrazoic acid, hydrohalogenic acid, ($C_1$-$C_6$)alkanoic acid, ($C_3$-$C_6$)alkenoic acid, halo($C_2$-$C_6$)alkanoic acid, halo($C_3$-$C_6$)alkenoic acid, phenyl($C_2$-$C_6$)alkanoic acid, phenoxy($C_2$-$C_6$)alkanoic acid, furanacetic acid, thiopheneacetic acid, benzoic acid, and symmetric acid anhydride;

acid salt selected from the group consisting of the alkali metal salt, alkaline earth metal salt, and a salt with an organic amine selected from the group consisting of ($C_1$-$C_6$)alkylamine, di($C_1$-$C_6$)alkylamine, tri($C_1$-$C_6$)alkylamine, aniline, pyridine, picoline, and N,N'-bis[phenyl($C_1$-$C_6$)alkyl]($C_1$-$C_6$)alkylenediamine, and $R^3$ is ($C_1$-$C_6$)alkyl, which consists essentially of: reacting a compound of the formula:

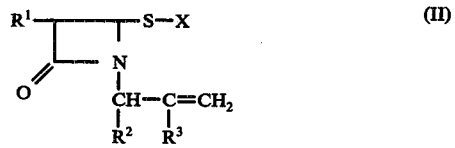

(II)

wherein $R^1$, $R^2$ and $R^3$ are each as defined above, and

X is a residue of a thiol compound selected from the group consisting of ($C_1$-$C_6$)alkylthio, ($C_2$-$C_6$)alkenylthio, ($C_1$-$C_6$)alkoxy($C_1$-$C_6$)alkylthio, phenyl($C_1$-$C_6$)alkylthio, xylyl($C_1$-$C_6$)alkylthio, halophenyl($C_1$-$C_6$)alkylthio, nitrophenyl($C_1$-$C_6$)alkylthio, mono- or di-($C_1$-$C_6$)alkoxyphenyl($C_1$-$C_6$)alkylthio, halo and ($C_1$-$C_6$)alkoxy substituted phenyl($C_1$-$C_6$)alkylthio, phenylthio, xylylthio, tolylthio, naphthylthio, mono- or di-halophenylthio, nitrophenylthio, mono- or di-($C_1$-$C_6$)alkoxyphenylthio, halo and nitro substituted phenylthio, heterocyclic thio wherein said heterocyclic group is selected from the group consisting of thienyl, furyl, pyrrolyl, pyridyl, imidazolyl, triazolyl, tetrazolyl, pyrrolidinyl, piperazinyl, piperidinyl, homopiperazinyl, quinolyl, isoquinolyl, benzimidazolyl, oxazolyl, oxadiazolyl, oxatriazolyl, thiazolyl, thiadiazolyl, thiatriazolyl, benzoxazolyl and benzothiazolyl, the above recited heterocyclic group having 1 to 6 substituents selected from the group consisting of ($C_1$-$C_6$)alkyl, ($C_1$-$C_6$)alkoxy, halogen, nitro, phenyl, tolyl, xylyl, halophenyl, nitrophenyl, and phenyl($C_1$-$C_6$)alkyl, with ammonia or an amine selected from the group consisting of ($C_1$-$C_6$)alkylamine, cyclo($C_5$-$C_8$)alkylamine, aniline, phenyl($C_1$-$C_6$)alkylamine, di($C_1$-$C_6$)alkylamine, diphenylamine, bis[phenyl($C_1$-$C_6$)alkyl]amine, pyrrolidine, piperidine, morpholine and 4-($C_1$-$C_6$)alkylpiperazine, in the presence of a metallic compound selected from the group consisting of silver acetate, mercury acetate, copper acetate, mercurous chloride, mercuric chloride, silver chloride, mercurous nitrate, and mercuric nitrate, which cleaves said thiol to produce a compound of the formula:

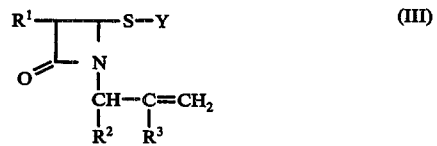

(III)

wherein $R^1$, $R^2$ and $R^3$ are each as defined above, and

Y is amino, $(C_1-C_6)$alkylamino, cyclo$(C_5-C_8)$alkylamino, anilino, phenyl$(C_1-C_6)$alkylamino, di$(C_1-C_6)$alkylamino, diphenylamino, bis[phenyl$(C_1-C_6)$alkyl]amino, 1-pyrrolidinyl, 1-piperidyl, morpholino or 4-$(C_1-C_6)$alkylpiperazin-1-yl, and cyclizing said compound (III) by a ring closure reaction in the presence of a condensing agent selected from the group consisting of $(C_1-C_6)$alkanoic acid, $(C_1-C_6)$alkanesulfonic acid, benzenesulfonic acid, toluenesulfonic acid, benzoic acid, hydrohalogenic acid, hydrazoic acid, carbonic acid, sulfuric acid, phosphoric acid, nitric acid, hydrocyanic acid, perchloric acid, boron trifluoride, a metal salt of the above recited acid wherein said metal is selected from the group consisting of alkali metal, alkaline earth metal, silver, copper, and mercury, mercury oxide, cuprous oxide, methyl iodide, an organic amine salt of the above recited acid wherein said organic amine is selected from the group consisting of $(C_1-C_6)$alkylamine, di$(C_1-C_6)$alkylamine, tri$(C_1-C_6)$alkylamine, aniline, toluidine, $(C_1-C_6)$alkylaniline, di$(C_1-C_6)$alkylaniline, pyridine, and picoline, alkali metal hydroxide, alkali metal $(C_1-C_6)$alkoxide, alkaline earth metal hydroxide, alkaline earth metal $(C_1-C_6)$alkoxide, $(C_1-C_6)$alkylamine, di$(C_1-C_6)$alkylamine, tri$(C_1-C_6)$alkylamine, aniline, $(C_1-C_6)$aniline, di$(C_1-C_6)$aniline, pyridine, picoline, 1,5-diazabicyclo[4,3,0]non-5-ene, 1,4-diazabicyclo[2,2,2]octane, 1,8-diazabicyclo[5,4,0]undecene-7, and Amberlite (trade mark) or with a polar solvent selected from the group consisting of formamide, dimethylformamide, dimethylacetamide, hexamethylphosphoric triamide, water, $(C_1-C_6)$alkanol, and dimethylsulfoxide at a temperature in the range of from room temperature to that resulting from the reaction mixture being heated to effect ring closure of compound (III).

3. A process for the preparation of a compound of the formula:

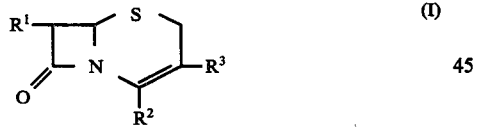

(I)

wherein
$R^1$ is amino;
$R^2$ is carboxy or protected carboxy, wherein said protected carboxy is an ester in which the ester moiety is selected from the group consisting of tri$(C_1-C_6)$alkylsilyl, $(C_1-C_6)$alkyl, cyclo$(C_3-C_8)$alkyl$(C_1-C_6)$alkyl, $(C_2-C_6)$alkenyl, $(C_2-C_6)$alkynyl, cyclo$(C_5-C_8)$alkyl, $(C_1-C_6)$alkoxy$(C_1-C_6)$alkyl, $(C_1-C_6)$alkylthio$(C_1-C_6)$alkyl, di$(C_1-C_6)$alkylamino, $(C_1-C_6)$alkylideneamino, $(C_1-C_6)$alkylsulfenyl$(C_1-C_6)$alkyl, phenyl, xylyl, tolyl, naphthyl, indanyl, dihydroanthryl, phenyl$(C_1-C_6)$alkyl, phenoxy$(C_1-C_6)$alkyl, phenylthio$(C_1-C_6)$alkyl, phenylsulfenyl$(C_1-C_6)$alkyl, $(C_1-C_6)$alkanoyloxy$(C_1-C_6)$alkyl, benzoyl$(C_1-C_6)$alkyl, phthalimido, pyridyl, piperidino, -pyridon-1-yl, tetrahydropyranyl, quinolyl, pyrazolyl, heterocyclic $(C_1-C_6)$alkyl, wherein said heterocyclic group is selected from the group consisting of pyridyl, piperidino, 2-pyridon-1-yl, tetrahydropyranyl, quinolyl, and pyrazolyl; the above recited protected carboxy ester having 1 to 10 substituents selected from the group consisting of $(C_1-C_6)$alkyl, $(C_1-C_6)$alkoxy, $(C_1-C_6)$alkylthio, $(C_1-C_6)$alkylsulfinyl, $(C_1-C_6)$alkanesulfonyl, phenylazo, halogen, cyano, hydroxy, and nitro;

acid amide selected from the group consisting of N-$(C_1-C_6)$alkyl acid amide, N,N-di$(C_1-C_6)$alkyl acid amide, N-phenyl acid amide, and acid amide with pyrazole, imidazole, 4-$(C_1-C_6)$alkylimidazole;

acid anhydride selected from the group consisting of acid anhydride of di$(C_1-C_6)$alkyl phosphate, debenzylphosphate, phosphoric acid halide, di$(C_1-C_6)$alkyl phophite, sulfurous acid, thiosulfuric acid, sulfuric acid, $(C_1-C_6)$alkyl carbonate, hydrazoic acid, hydrohalogenic acid, $(C_1-C_6)$alkanoic acid, $(C_3-C_6)$alkenoic acid, halo$(C_2-C_6)$alkanoic acid, halo$(C_3-C_6)$alkenoic acid, phenyl$(C_2-C_6)$alkanoic acid, phenoxy$(C_2-C_6)$alkanoic acid, furanacetic acid, thiopheneacetic acid, benzoic acid, and symmetric acid anhydride;

acid salt selected from the group consisting of the alkali metal salt, alkaline earth metal salt, and a salt with an organic amine selected from the group consisting of $(C_1-C_6)$alkylamine, Di$(C_1-C_6)$alkylamine, tri$(C_1-C_6)$alkylamine, aniline, pyridine, picoline, and N,N'-bis[phenyl$(C_1-C_6)$alkyl]$(C_1-C_6)$alkylenediamine, and $R^3$ is $(C_1-C_6)$alkyl,
which consists essentially of: reacting a compound of the formula:

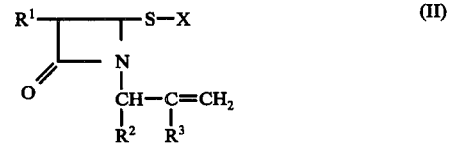

(II)

wherein $R^1$, $R^2$ and $R^3$ are each as defined above, and X is a residue of a thiol compound selected from the group consisting of $(C_1-C_6)$alkylthio, $(C_2-C_6)$alkenylthio, $(C_1-C_6)$alkoxy$(C_1-C_6)$alkylthio, phenyl$(C_1-C_6)$alkylthio, xylyl$(C_1-C_6)$alkylthio, halophenyl$(C_1-C_6)$alkylthio; nitrophenyl$(C_1-C_6)$alkylthio, mono- or di-$(C_1-C_6)$alkoxyphenyl$(C_{1-C6})$alkylthio, halo and $(C_1-C_6)$alkoxy substituted phenyl$(C_1-C_6)$alkylthio, phenylthio, xylylthio, tolylthio, naphthylthio, mono- or dihalophenylthio, nitrophenylthio, mono- or di-$(C_1-C_6)$alkoxyphenylthio, halo and nitro substituted phenylthio, heterocyclic thio wherein said heterocyclic group is selected from the group consisting of thienyl, furyl, pyrrolyl, pyridyl, imidazolyl, triazolyl, tetrazolyl, pyrrolidinyl, piperazinyl, piperidinyl, homopiperazinyl, quinolyl, isoquinolyl, benzimidazolyl, oxazolyl, oxadiazolyl, oxatriazolyl, thiazolyl, thiadiazolyl, thiatriazolyl, benzoxazolyl and benzothiazolyl, the above recited heterocyclic group having 1 to 6 substituents selected from the group consisting of $(C_1-C_6)$alkyl, $(C_1-C_6)$alkoxy, halogen nitro, phenyl, tolyl, xylyl, halophenyl, nitrophenyl, and phenyl$(C_1-C_6)$alkyl, with a condensing agent selected from the group consisting of $(C_1-C_6)$alkanoic acid, $(C_1-C_6)$alkanesulfonic acid, benzenesulfonic acid, tolunesulfonic acid, benzoic acid, hydrohalogenic acid, hydrazoic acid, carbonic acid, sulfuric acid, phosphoric acid, nitric acid, hydrocyanic acid, perchloric acid, boron trifluoride, a metal salt of the above recited acid wherein said metal is selected from the group consisting of alkali metal, alkaline earth metal, silver, copper, and mercury, mercury oxide, cuprous oxide, methyl iodide, an organic amine salt of the above recited acid wherein said organic amine is selected from the group consisting of $(C_1-C_6)$alkylamine, di$(C_1-C_6)$alkylamine, tri$(C_1-C_6)$alkylamine, aniline, toluidine, $(C_1-C_6)$alkylaniline, di$(C_1-C_6)$alkylaniline, pyridine, and picoline, alkali metal hydroxide, alkali metal $(C_1-C_6)$alkoxide, alkaline earth metal hydroxide, alkaline earth metal $(C_1-C_6)$alkoxide, $(C_1-C_6)$alkylamine, di$(C_1-C_6)$alkylamine, tri$(C_1-C_6)$alkylamine, aniline, $(C_1-C_6)$aniline, di$(C_1-C_6)$aniline, pyridine, picoline, 1,5-diazabicyclo[4,3,0]non-5-ene, 1,4-diazabicyclo[2,2,2]octane, 1,8-diazabicyclo[5,4,0]undecene-7, and Amberlite (trademark) or
with a polar solvent selected from the group consisting of formamide, dimethylformamide, dimethylacetamide, hexamethylphosphoric triamide, water, $(C_1-C_6)$-alkanol, and dimethylsulfoxide at a temperature in the range of from room temperature to that resulting from the reaction mixture being heated to effect ring closure of compound (II).

4. A process for the preparation of a compound of the formula:

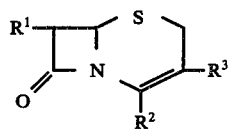 (I)

wherein
$R^1$ is amino;
$R^2$ is carboxy or protected carboxy, wherein said protected carboxy is an ester in which the ester moiety is selected from the group consisting of tri$(C_1-C_6)$alkylsilyl, $(C_1-C_6)$alkyl, cyclo$(C_3-C_8)$alkyl$(C_1-C_6)$alkyl, $(C_2-C_6)$alkenyl, $(C_2-C_6)$alkynyl, cyclo$(C_5-C_8)$alkyl, $(C_1-C_6)$alkoxy$(C_1-C_6)$alkyl, $(C_1-C_6)$alkylthio$(C_1-C_6)$alkyl, di$(C_1-C_6)$alkylamino, $(C_1-C_6)$alkylidenamino, $(C_1-C_6)$alkylsulfenyl$(C_1-C_6)$alkyl, phenyl, xylyl, tolyl, naphthyl, indanyl, dihydroanthryl, phenyl$(C_1-C_6)$alkyl, phenoxy$(C_1-C_6)$alkyl, phenylthio$(C_1-C_6)$alkyl, phenylsulfenyl$(C_1-C_6)$alkyl, $(C_1-C_6)$alkanoyloxy$(C_1-C_6)$alkyl, benzoyl$(C_1-C_6)$alkyl, phthalimido, pyridyl, piperidino, 2-pyridon-1-yl, tetrahydropyranyl, quinolyl, pyrazolyl, heterocyclic $(C_1-C_6)$alkyl, wherein said heterocyclic group is selected from the group consisting of pyridyl, piperidino, 2-pyridon-1-yl, tetrahydropyranyl, quinolyl, and pyrazolyl; the above recited protected carboxy ester having 1 to 10 substituents selected from the group consisting of $(C_1-C_6)$alkyl, $(C_1-C_6)$alkoxy, $(C_1-C_6)$alkylthio, 1$(C_1-C_6)$alkylsulfinyl, $(C_1-C_6)$alkanesulfonyl, phenylazo, halogen, cyano, hydroxy, and nitro;
acid amide selected from the group consisting of N-$(C_1-C_6)$alkyl acid amide, N,N-di$(C_1-C_6)$alkyl acid amide, N-phenyl acid amide, and acid amide with pyrazole, imidazole, 4-$(C_1-C_6)$alkylimidazole; acid anhydride selected from the group consisting of acid anhydride of di$(C_1-C_6)$alkyl phosphate, dibenzylphosphate, phosphoric acid halide, di$(C_1-C_6)$alkyl phophite, sulfurous acid, thiosulfuric acid, sulfuric acid, $(C_1-C_6)$alkyl carbonate, hydrazoic acid, hydrohalogenic acid, $(C_1-C_6)$alkanoic acid, $(C_3-C_6)$alkenoic acid, halo$(C_2-C_6)$alkanoic acid halo$(C_3-C_6)$alkenoic acid, phenyl$(C_2-C_6)$alkanoic acid, phenoxy$(C_2-C_6)$alkanoic acid, furanacetic acid, thiopheneacetic acid, benzoic acid, and symmetric acid anhydride;
acid salt selected from the group consisting of the alkali metal salt, alkaline earth metal salt, and a salt with an organic amine selected from the group consisting of $(C_1-C_6)$alkylamine, di$(C_1-C_6)$alkylamine, tri$(C_1-C_6)$alkylamine, aniline, pyridine, picoline, and N,N'-bis[phenyl$(C_1-C_6)$alkyl]$(C_1-C_6)$alkylenediamine, and
$R^3$ is $(C_1-C_6)$alkyl, consists essentially of: reacting a compound of the formula:

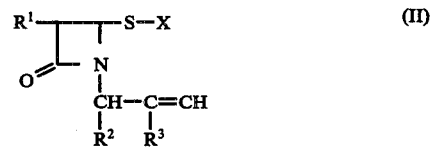 (II)

wherein $R^1$, $R^2$ and $R^3$ are each as defined above, and X is a residue of a thiol compound selected from the group consisting of $(C_1-C_6)$alkylthio, $(C_2-C_6)$alkenylthio, $(C_1-C_6)$alkoxy$(C_1-C_6)$alkylthio, phenyl$(C_1-C_6)$alkylthio, xylyl$(C_1-C_6)$alkylthio, halophenyl$(C_1-C_6)$alkylthio; nitrophenyl$(C_1-C_6)$alkylthio, mono- or di-$(C_1-C_6)$alkoxyphenyl$(C_1-C_6)$alkylthio, halo and $(C_1-C_6)$alkoxy substituted phenyl$(C_1-C_6)$alkylthio, phenylthio, xylylthio, tolylthio, naphthylthio, mono- or dihalophenylthio, nitrophenylthio, mono- or di-$(C_1-C_6)$alkoxyphenylthio, halo and nitro substituted phenylthio, heterocyclic thio wherein said heterocyclic group is selected from the group consisting of thienyl, furyl, pyrrolyl, pyridyl, imidazolyl, triazolyl, tetrazolyl, pyrrolidinyl, piperazinyl, piperidinyl, homopiperazinyl, quinolyl, isoquinolyl, benzimidazolyl, oxazolyl, oxadiazolyl, oxatrizolyl, thiazolyl, thiadiazolyl, thiatriazolyl, benzoxazolyl and benzothiazolyl,
the above recited heterocyclic group having 1 to 6 substituents selected from the group consisting of $(C_1-C_6)$alkyl, $(C_1-C_6)$alkoxy, halogen, nitro, phenyl, tolyl, xylyl, halophenyl, nitrophenyl, and phenyl$(C_1-C_6)$alkyl, with ammonia or an amine selected from the group consisting of $(C_1-C_6)$alkylamine, cyclo$(C_5-C_8)$alkylamine, aniline, phenyl$(C_1-C_6)$alkylamine, di$(C_1-C_6)$alkylamine, diphenylamine, bis[phenyl$(C_1-C_6)$alkyl]amine, pyrrolidine, piperidine, morpholine and 4-$(C_1-C_6)$ alkylpiperazine, in the presence of a metallic compound selected from the group consisting of silver acetate, mercury acetate, copper acetate, mercurous chloride, mercuric chloride, silver chloride, mercurous nitrate, and mercuric nitrate, which cleaves said thiol to produce a compound of the formula:

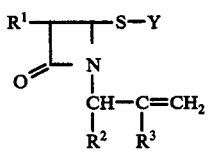 (III)

wherein R¹, R² and R³ are each as defined above, and Y is amino, $(C_1-C_6)$alkylamino, cyclo$(C_5-C_8)$alkylamino, anilino, phenyl$(C_1-C_6)$alkylamino, di$(C_1-C_6)$alkylamino, diphenylamino, bis[phenyl$(C_1-C_6)$alkyl]amino, 1-pyrrolidinyl, 1-piperidyl, morpholino or 4-$(C_1-C_6)$alkylpiperazin-1-yl, and cyclizing said compound (III) by a ring closure reaction in the presence of a condensing agent selected from the group consisting of $(C_1-C_6)$alkanoic acid, $(C_1-C_6)$alkanesulfonic acid, benzenesulfonic acid, tolunesulfonic acid, benzoic acid, hydrohalogenic acid, hydrazoic acid, carbonic acid, sulfuric acid, phosphoric acid, nitric acid, hydrocyanic acid, perchloric acid, boron trifluoride, a metal salt of the above recited acid wherein said metal is selected from the group consisting of alkali metal, alkaline earth metal, silver, copper, and mercury, mercury oxide, cuprous oxide, methyl iodide, an organic amine salt of the above recited acid wherein said organic amine is selected from the group consisting of $(C_1-C_6)$alkylamine, di$(C_1-C_6)$alkylamine, tri$(C_1-C_6)$alkylamine, aniline, toluidine, $(C_1-C_6)$alkylaniline, di$(C_1-C_6)$alkylaniline, pyridine, and picoline, alkali metal hydroxide, alkali metal $(C_1-C_6)$alkoxide, alkaline earth metal hydroxide, alkaline earth metal $(C_1-C_6)$alkoxide, $(C_1-C_6)$alkylamine, di$(C_1-C_6)$alkylamine, tri$(C_1-C_6)$alkylamine, aniline, $(C_1-C_6)$aniline, di$(C_1-C_6)$aniline, pyridine, picoline, 1,5-diazabicyclo[4,3,0]non-5-ene, 1,4-diazabicyclo[2,2,2]octane, 1,8-diazabicyclo[5,4,0]undecene-7, and Amberlite (trade mark) or with a polar solvent selected from the group consisting of formamide, dimethylformamide, dimethylacetamide, hexamethylphosphoric triamide, water, $(C_1-C_6)$-alkanol, and dimethylsulfoxide at a temperature in the range of from room temperature to that resulting from the reaction mixture being heated to effect ring closure of compound (III).

* * * * *